US006423296B1

(12) United States Patent
Gunther et al.

(10) Patent No.: US 6,423,296 B1
(45) Date of Patent: *Jul. 23, 2002

(54) CONSTRAST MEDIA

(75) Inventors: Wolfgang Gunther, West Chester; Kenneth Kellar, Wayne; Dennis Kiyoshi Fujii, Downingtown; Vinay Desai; Christopher Black, both of Wayne; Marshall Beeber, Royersford; Jennifer Wellons, Wayne, all of PA (US); Anne Kjersti Fahlvik, Oslo (NO); Jasbir Singh, Gilbertsville, PA (US); Edward Richard Bacon, Wayne, PA (US); Gregory Lynn McIntire, Wayne, PA (US); Robert Alan Snow, Wayne, PA (US); Brian Weekley, Wayne, PA (US); Torgrim Engell, Oslo; Michel Gacek, Hovik, both of (NO); David Lee Ladd, Wayne, PA (US); Anne Naevestad, Oslo (NO); George Na, Wayne, PA (US); Barbara Yuan, Wayne, PA (US); Jack Stevens, Wayne, PA (US)

(73) Assignee: Amersham Health AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/101,528

(22) PCT Filed: Jan. 9, 1997

(86) PCT No.: PCT/GB97/00067

§ 371 (c)(1),
(2), (4) Date: Feb. 22, 1999

(87) PCT Pub. No.: WO97/25073

PCT Pub. Date: Jul. 17, 1997

Related U.S. Application Data

(63) Continuation-in-part of application No. 08/729,836, filed on Oct. 15, 1996, now Pat. No. 6,123,920.

(30) Foreign Application Priority Data

Jan. 10, 1996 (GB) ............................................. 9600427

(51) Int. Cl.$^7$ ............................................. A61B 5/055
(52) U.S. Cl. .................... 424/9.322; 424/9.3; 424/9.32; 424/9.1
(58) Field of Search .............................. 424/9.32, 9.322, 424/1.11, 9.1, 9.3; 600/420

(56) References Cited

U.S. PATENT DOCUMENTS

| 3,935,187 A | 1/1976 | Speakman ........... 260/233.3 R |
| 4,101,435 A | 7/1978 | Hasegawa et al. ........ 424/9.322 |
| 4,335,094 A | 6/1982 | Mosbach |
| 4,357,259 A | 11/1982 | Senyei et al. ................. 264/4.3 |
| 4,452,773 A | 6/1984 | Molday |
| 4,501,726 A | 2/1985 | Schroder |
| 4,647,447 A | 3/1987 | Gries et al. |
| 4,675,173 A | 6/1987 | Widder |
| 4,731,239 A | 3/1988 | Gordan |
| 4,735,796 A | 4/1988 | Gordon |
| 4,770,183 A | 9/1988 | Groman et al. ............. 424/9.32 |
| 4,795,698 A | 1/1989 | Owen et al. |
| 4,827,945 A | 5/1989 | Groman et al. ............. 424/9.32 |
| 4,863,715 A | 9/1989 | Jacobsen et al. |
| 4,871,716 A | 10/1989 | Longo et al. ............. 424/9.322 |
| 4,879,210 A | 11/1989 | Widder |
| 4,904,479 A | 2/1990 | Illum |
| 4,951,675 A | 8/1990 | Groman et al. ............. 424/9.32 |
| 5,055,288 A | 10/1991 | Lewis et al. ................ 424/9.32 |
| 5,069,216 A | 12/1991 | Groman et al. ............. 424/9.32 |
| 5,102,652 A | 4/1992 | Groman et al. ............. 424/9.32 |
| 5,114,703 A | 5/1992 | Wolf et al. |
| 5,160,725 A | 11/1992 | Pilgrimm |
| 5,204,445 A | 4/1993 | Maruno et al. ............. 536/101 |
| 5,219,554 A | 6/1993 | Groman et al. ............. 424/9.32 |
| 5,225,282 A | 7/1993 | Chagnon et al. ............ 428/407 |
| 5,248,492 A | 9/1993 | Groman et al. ............. 424/9.32 |
| 5,262,176 A | 11/1993 | Palmacci et al. |
| 5,284,646 A | 2/1994 | Menz et al. ............. 424/9.322 |
| 5,314,679 A | 5/1994 | Lewis et al. ................ 424/9.32 |
| 5,328,681 A | 7/1994 | Kito et al. |

(List continued on next page.)

FOREIGN PATENT DOCUMENTS

| EP | 0 186 616 | 11/1985 |
| EP | 0 580 878 A1 | 6/1992 |
| EP | 0 656 368 A1 | 2/1994 |
| WO | WO 85/02772 | 4/1985 |
| WO | WO 86/01112 | 6/1985 |
| WO | WO 88/07365 | 10/1988 |
| WO | WO 89/03675 | 5/1989 |
| WO | WO 89/1154 | 11/1989 |
| WO | WO 91/02811 | 3/1991 |
| WO | WO 91/12025 | 8/1991 |
| WO | WO 92/11037 | 7/1992 |
| WO | WO 94/02068 | 2/1994 |
| WO | WO 94/04197 | 3/1994 |
| WO | WO 94/21240 | 9/1994 |
| WO | WO 95/31220 | 11/1995 |
| WO | WO 96/09840 | 4/1996 |

OTHER PUBLICATIONS

Bach–Gansmo T, Fahlvik AK, Ericsson A, Hemmingsson A. Superparamagnetic iron oxide for liver imaging. Comparison among three different preparations. Invest. Radiol. 1994 29(3):339–344.

(List continued on next page.)

Primary Examiner—Dameron L. Jones
(74) Attorney, Agent, or Firm—Bacon & Thomas

(57) ABSTRACT

The invention relates to MR contrast media containing composite nanoparticles, preferably comprising a superparamagnetic iron oxide core provided with a coating comprising an oxidatively cleaved starch coating optionally together with a functionalized polyalkyleneoxide which serves to prolong blood residence.

13 Claims, 1 Drawing Sheet

U.S. PATENT DOCUMENTS

| | | | |
|---|---|---|---|
| 5,342,607 A | 8/1994 | Josephson | |
| 5,349,957 A | 9/1994 | Yudelson | |
| 5,352,432 A | 10/1994 | Menz et al. | |
| 5,358,702 A | 10/1994 | Unger | 424/9.322 |
| 5,368,840 A | 11/1994 | Unger | 424/9 |
| 5,382,468 A | 1/1995 | Lewis et al. | 424/9.32 |
| 5,411,730 A | 5/1995 | Kirpotin et al. | 424/9.322 |
| 5,424,419 A | 6/1995 | Hasegawa et al. | 424/9.322 |
| 5,427,767 A | 6/1995 | Kresse et al. | 424/9.32 |
| 5,464,696 A | 11/1995 | Tournier et al. | |
| 5,496,536 A | 3/1996 | Wolf | |
| 5,512,332 A | 4/1996 | Liberti et al. | |
| 6,123,920 A * | 9/2000 | Gunther et al. | 424/9.322 |

OTHER PUBLICATIONS

Chouly C. Pouliquen D, Lucet I, Juene JJ, Jallet P. Development of superaramagnetic nanoparticles for MRI: effect of particle size, charge and surface nature on biodistribution. J. Microencapsulation 1996 13(3):245–255.

Fahlvik AK, Holtz E, Klaveness J. Relaxation efficacy of paramagnetic and superparamagnetic microspheres in liver and spleen. Magn. Reson. Imaging 1990 8:363–369.

Fahlvik AK, Holtz E, Leander P, Schroder U, Klaveness J. Magnetic starch microspheres: efficacy and elimination: a new organ–specific contrast agent for magnetic resonence imaging. Invest. Radiol. 1990 25: 113–120.

Cerdan S, Lotscher HR, Kunnecke B, Seelig J. Monoconal antibody–coated magnetite particles as contrast agents in magnetic resonance imaging of tumors. Magn. Reson. Med. 1989 12:151–163.

Fahlvik Ak, Naevestad A, Ege T, Froysa A, Sonstevoid A, Strande P, Ostensen J. Significance of surface properties in the devlopment of biocompatible iron oxide contrast agents. Proceedings of the 4th Special Top Seminar of the European Magnetic Resonance Forum. Santiago de Compostela, Spain Sep. 28–30, 1994 pp. 105–116.

Fahlvik AK, Artusson P, Edman P. Magnetic starch microspheres: interactions of a microsphere MR contrast medium with macrophages in vitro. Int. J. Pharm. 1990 65(3):249–259.

Fahlvik AK, Holtz E, Schroder U, Klaveness J. Magnetic starch microspheres, biodistribution and biotransformation. A new organ –specific contrast agent for magnetic resonance imaging. Invest. Radiol. 1990 25(7):793–797.

Gunderson HG, Bach–Gansmo T, Holtz E, Fahlvik AK, Aune O, Berg A. Superparamagnetic contrast agents for magnetic resonance imaging. Invest. Radiol. 1990 25(Suppl. 1):S67–S68.

Thomassen T, Nordby Wiggen U, Gundersen HG, Fahlvik AK, Aune O, Klaveness J. Structure activity relationship of magnetic particles as MR contrast agents. Magn. Reson. ImG. 1991 9:255–258.

Colet JM, Muller RN. Effect of opsinins on the uptake of magnetic starch microspheres by rat kupffer cells, MAGMA 1994 2:303–305.

Furusawa K, Nagashima K, Anzai C. Synthetic process to control the total size and component distribution of multi-layer magnetic composite particles. Coll. Polym. Sci. 1994 272:1104–1110.

Lee J, Isobe T, Senna M. Preparation of ultrafine $Fe_3O_4$ particles by precipitation in presnece of PVA at high pH. J. Coll. INterf. Sci. 1996 177:490–494.

Mann S, et al. Crystallization at inorganic–organic interfaces: biominerals and biomimetic synthesis. Science 1993 261:1286–1292.

Shinkai M, Honda H, Koobayashi T. Preparation of fine magnetic particles and application for enzyme immobilization. Biocatalysis 1991 5:61–69.

Synthesis of nanoscale iron oxide structures using protein cages and polysaccharide networks. NATO ASI Ser. Ser E 1994 260:49–56.

Autio et al., "Heat–induced structural changes of acid–hydrolysed and hyperchlorite–oxidized barley starches" Carbohydrate Polymers, 29(3):155–161, 1996.

Hasegawa et al., "Adsorption behaviour of oxidised starch onto iron or alumninium", Chem. Abs. 70(12), Abs. No. 050898, 1969.

Kresse et al., "Magnetopharmaka", Deutsche Apotheker Zeitung, 134(33), 1994.

Parovouri et al., "Oxidation of potato starch by hydrogen peroxide", Starch, 47(1):19–23, 1995.

Wang et al., "Development of cold–setting starch adhesive", Chem. Abs. 115(10), Abs. No. 093953, 1991.

* cited by examiner

CONTRAST MEDIA

This is a continuation of international patent application no. PCT/GB97/00067, with an international filing date of Jan. 9, 1997, now pending and a continuation-in-part of application Ser. No. 08/729,836, filed Oct. 15, 1996, now U.S. Pat. No. 6,123,920.

FIELD OF THE INVENTION

This invention relates to superparamagnetic particulate contrast agents, in particular for use in magnetic resonance imaging, especially of the vasculature, and to their preparation.

BACKGROUND TO THE INVENTION

In diagnostic imaging modalities, such as X-ray, ultrasound and magnetic resonance (MR) imaging for example, the use of contrast agents to enhance contrast between different tissues or organs or between healthy and damaged tissue is a well established technique. For the different imaging modalities, contrast enhancement by the contrast agent is achieved in different ways. Thus in proton MR imaging for example contrast agents generally achieve their contrast enhancing effect by modifying the characteristic relaxation times ($T_1$ and $T_2$) of the imaging nuclei (generally water protons) from which the MR signal which is used to generate the image derives.

When injected into a living being, materials with magnetic properties such as paramagnetism, superparamagnetism, ferromagnetism and ferrimagnetism can cause a reduction in the $T_1$ and $T_2$ (or $T_2^*$) values of tissue water protons. Although a reduction in $T_1$ cannot occur without a reduction in $T_2$ (or $T_2^*$), the fractional decrease in $T_1$ can be different from that in $T_2$ (or $T_2^*$). If the fractional decrease in $T_1$ is greater than that in $T_2$ (or $T_2^*$) then the intensity of the MR image increases, and the material is referred to as a $T_1$, or positive, contrast agent. If the fractional decrease in $T_1$ is less than that in $T_2$ (or $T_2^*$) then the intensity of the MR image decreases, and the material is referred to as a $T_2$ (or $T_2^*$), or negative, contrast agent.

Particles with the magnetic properties of superparamagnetism, ferrimagnetism and ferromagnetism are referred to herein as magnetic particles.

The first suggestion in the literature for the use of magnetic materials as MR contrast agents was the proposal in 1978 by Lauterbur that manganese salts might be used in this regard. The first proposal in the patent literature was the suggestion by Schering in EP-A-71564 (and its equivalent U.S. Pat. No. 4,647,447) that chelate complexes of paramagnetic metal ions, such as the lanthanide ion Gd(III), might be used.

The early commercial contrast agents for MR imaging, such as GdDTPA, GdDTPA-BMA and GdHP-D03A available from Schering, Nycomed and Bracco under the trade marks MAGNEVIST, OMNISCAN and PROHANCE, are all soluble chelate complexes of paramagnetic lanthanide ions and in use are positive contrast agents which enhance image intensity from the regions to which they distribute.

Subsequently, particulate ferromagnetic, ferrimagnetic and superparamagnetic agents were proposed for use as negative MR contrast agents. Oral formulations of such particulate agents, generally referred to herein as magnetic particles, have become available commercially for imaging of the gastrointestinal tract, e.g. the product ABDOSCAN available from Nycomed Imaging. However parenteral administration of such particulate agents has also been widely proposed for imaging of the liver and spleen as these organs act to remove foreign particulate matter from the blood relatively rapidly. Thus, by way of example, liver and spleen imaging using such agents is proposed by Widder in U.S. Pat. No. 4,859,210.

More recently it has been proposed, for example by Pilgrimm in U.S. Pat. No. 5,160,725 and WO-94/21240, that the uptake of parenterally administered magnetic particles from the blood by the reticuloendothelial system may be hindered, and thus blood residence time prolonged, by chemically binding a stabilizer substance to the magnetic particle surface.

Examples of materials which may be used in this way as stabilizers include carbohydrates such as oligo- and polysaccharides, as well as polyamino acids, oligo- and polynucleotides and polyalkylene oxides (including poloxamers and poloxamines) and other materials proposed by Pilgrimm in U.S. Pat. No. 5,160,725 and WO-94/21240, by Nycomed in PCT/GB94/02097, by Bracco in U.S. Pat. No. 5,464,696 and by Illum in U.S. Pat. No. 4,904,479.

Magnetic particles coated in this fashion can then be used as blood pool agents (i.e. for imaging the vasculature) or for lymph node imaging, or alternatively they may be conjugated to biotargeting agents and used for imaging the targeted tissues or organs.

When administered as blood pool agents, it has been found with magnetic particles that the fractional reduction in $T_1$ of the blood protons can be greater than the fractional decrease in $T_2$ (or $T_2^*$) and thus such agents can be used as positive MR agents for the vasculature.

For parenteral use, the size and size distribution of the composite particles and the chemical nature of the surface of the overall particle are of great importance in determining the contrast generation efficacy, the blood half-life, and the biodistribution and biodegradation of the contrast agent. Ideally the magnetic particle size (i.e. the crystal size of the magnetic material) is within the single domain size range (such that the particles are superparamagnetic and thus have no hysteresis and a reduced tendency to aggregate) and the overall particle size distribution is narrow so that the particles have uniform biodistribution, bioelimination and contrast effects. Preferably, the magnetic particles should be provided with a surface coating of a material which modifies particle biodistribution, e.g. by prolonging blood half-life, or by increasing stability, or which acts as a targetting vector causing preferential distribution to a target site, such as a tumour site.

Mean crystal sizes, i.e. of the magnetic core material, should generally be in the range 1 to 50 nm, preferably 1 to 20 nm and especially preferably 2 to 15 nm and, for use as blood pool agents, the mean overall particle size including any coating material should preferably be below 30 nm. (Particle size can be determined by electron microscopy). Producing superparamagnetic crystals or composite particles having such sizes is not in itself particularly problematical. However producing particles with the desired size, acceptable size distribution and without undue crystal aggregation does represent a problem and it is to the solution of this problem that one aspect of the present invention is directed.

Typically, the magnetic crystals are produced by liquid phase precipitation, generally in a solution of a polymeric coating agent (e.g. using a co-precipitation technique such as that described by Molday in U.S. Pat. No. 4,452,773). This technique results in the generation of relatively polydisperse particles which require a subsequent size fractionation step, e.g. by centrifugation or chromatography. By way of example it is by such a technique that the product AMI 227 of Advanced Magnetics is produced.

We have now found that magnetic particles with particularly advantageous properties can be produced by precipitation in a branched polymer containing aqueous medium and subsequently cleaving the polymer to release composite particles comprising magnetic particles and a cleaved polymer coating.

SUMMARY OF THE INVENTION

Thus viewed from one aspect the invention provides a process for producing composite magnetic particles, said process comprising:

forming magnetic particles, preferably superparamagnetic particles, within a hydrophilic branched organic polymer containing aqueous medium; and cleaving said polymer whereby to release said composite particles, the majority preferably containing a single magnetic particle.

DETAILED DESCRIPTION OF THE INVENTION

Figure 1:
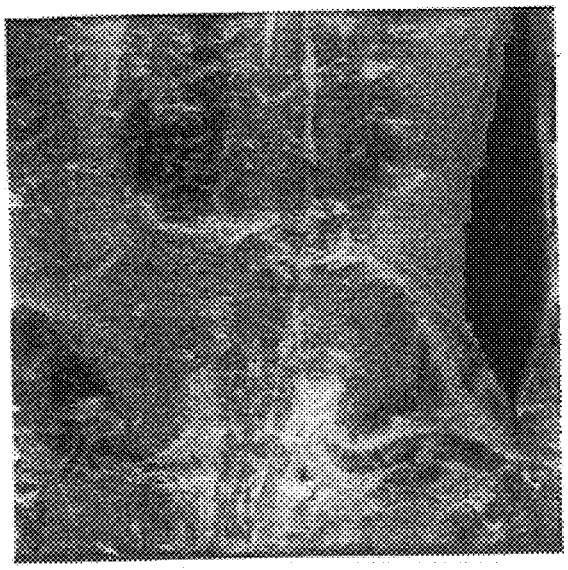
FIGS. 1, 2 and 3 show pre- and post contrast $T_1$-weighted MR images of the rabbit following administration of a contrast medium according to the invention.

The hydrophilic branched organic polymer used in the process of the invention may be any natural, synthetic or semi-synthetic branched polymer and may if desired be produced by grafting to or cross-linking a linear hydrophilic polymer.

Where the branched hydrophilic polymer is an extensively cross-linked polymer, the cleavage of the polymer in the process of the invention will result in a breakdown of the cross-linked polymer matrix. It is preferred therefore that the cross-linking bonds should be susceptible to chemical or biochemical cleavage under conditions which do not cause significant degradation of the magnetic particles. Ester-cross-linked hydrogel-forming polymers (for example formed by cross-linking hydroxy group bearing polymers such as linear carbohydrates (e.g. dextran) or polyvinylalcohol) are thus particularly suitable candidates for such cross-linked polymers. If necessary, the polymers may be appropriately substituted to allow control over the ester cleavage rate. Ester cleavage in this regard may be by base treatment, e.g. with ammonia or an alkali metal hydroxide.

Nonetheless, in the process of the invention, the hydrophilic branched polymer is especially preferably a natural, synthetic or semi-synthetic carbohydrate, particularly a material capable of forming an aqueous gel and more preferably a polysaccharide material, e.g. a glycogen, or even more preferably a starch. If desired, in the process of the invention one may use a mixture of hydrophilic polymers at least one of which is branched. Where a starch is used as the polymer this may be a native starch or alternatively a processed starch, e.g. an acid-treated, enzyme-treated or solubilized starch. Natural starches, especially plant-derived starches such as corn, potato, rice or wheat starch, are particularly preferred.

Natural starches are a combination of the generally linear amylose and the branched amylopectin polysaccharides. For the practice of the invention, while amylose content is acceptable it is preferably not so high as to cause retrogradation, the largely irreversible transition from dispersed state to essentially insoluble microcystalline state. For this reason the use of the amylopectin rich potato starch is preferred to maize or wheat starches.

Where the polymer material used according to the invention is a material which is affected by dissolution in an aqueous medium and heat treatment therein, e.g. a material such as starch which from a granular state first swells and partially dissolves, the thermal history of the reaction medium may affect the properties of the final product. In such cases, a thermal history which leads to greater control of the viscosity and structure of the medium may be preferable. Thus for starch in particular it is preferred that the reaction medium is created, cooled and then reheated, e.g. by formation of an aqueous dispersion at 60–95° C., cooling to between 5 and 80° C. (e.g. 5 to 60° C.) and reheating to 45 to 85° C. (e.g. 45 to 80° C.). In this way, an advantageous structure for the precipitation medium may be achieved.

It is believed that the branched hydrophilic organic polymer provides dispersed precipitation seeding sites within the aqueous medium allowing uniform small precipitate particles to form. The use of non-branched hydrophilic polymers, such as gelatin or dextran, or of inorganic gels such as silica gel, is not effective.

The hydrophilic branched polymer is preferably present at a concentration sufficient to cause the precipitation medium to be in gel form at ambient or periambient temperatures, e.g. 0 to 60° C. The concentration used is also conveniently such as to produce a gel at temperatures up to 80° C. For starches, concentrations of 1 to 200 g/L, especially 2 to 150 g/L, particularly 20 to 100 g/L, and more particularly 40 to 90 g/L, are preferred.

While the precipitation medium is aqueous, it may also contain mixtures of water and co-solvents such as water-miscible alcohols, ethers or ketones.

As indicated above, it is particularly preferred that the precipitation medium used according to the invention be in the colloidal state of matter referred to as a gel. In such a medium polymeric gel forming material forms a network which is interpenetrated by the aqueous dispersion medium. Such a gel will generally be more viscous than the aqueous dispersion medium alone but for the purposes of the invention the gel need not be so viscous as to be in a rigid or semi-rigid self-supporting state. Indeed the gel structure may even be so weak that the precipitation medium may seem simply to be a free flowing solution. However in that event, the gel nature of the medium may readily be verified by its thixotropic properties, namely that the viscosity of the medium is reduced by agitation.

While the precipitation medium must contain a branched polymer as mentioned above, it may contain other gel forming polymers which may for example be linear. Examples of suitable polymers for use in this regard include proteins, polysaccharides, proteoglycans and gel forming surfactants, for example block copolymer surfactants of the Pluronic and Tetronic series such as F-127, F-108 and F-68. These surfactants form gels in aqueous media at the elevated temperatures and pH levels useful in the process of the present invention. Thus by way of example a precipitation medium in gel form may be prepared using an aqueous dispersion of a gel-forming linear block copolymer surfactant and a branched organic polymer such as amylopectin.

The gel matrix of the precipitation medium however should be such as to allow chemical (or biochemical)

scission of at least one of the polymer components, preferably at least the branched polymer, so as to release the magnetic particles. For this reason, the use of heavily cross-linked polymers is not desirable.

Particle precipitation may be effected with the aqueous medium in rigid or semi-rigid gel form, e.g. by permeating the gel with a base, but most preferably precipitation is effected in a heated, agitated (e.g. stirred) aqueous medium which may or may not exhibit noticeably enhanced viscosity relative to water. Particularly preferably precipitation is effected at temperatures in the range 40 to 95° C., and with gentle stirring.

By manipulating the thixotropic properties of the aqueous precipitation medium, composite particles according to the invention having a range of sizes can be produced.

It is believed that magnetic particle formation in the process of the invention may be a two-stage process with domains of amorphous material forming and then transforming into magnetic particles, e.g. at an elevated temperature, for example 40 to 95° C., preferably 50 to 93° C. Thus it has been found that the development of the magnetic properties of the particles can be monitored over a period of minutes to hours, e.g. up to 3 hours. However, in practice it is found that development of magnetic properties is substantially complete within two hours and that significant magnetization is developed within twenty minutes.

The magnetic particles which form in the aqueous medium may be of any precipitable magnetic metal oxide or oxide hydroxide, including mixed metal compounds, for example compounds as discussed in U.S. Pat. No. 4,827,945 (Groman), EP-A-525189 (Meito Sangyo), EP-A-580878 (BASF) and PCT/GB94/02097 (Nycomed) or by Pilgrimm (supra). Particular mention in this regard may be made of magnetic iron oxide compounds of formula $$(M''O)_n(M'''_2O_3)$$

where $M''$ and $M'''$ are transition or lanthanide metals in the II or III valence state, at least one of which is Fe, and n is zero or a positive number, or more particularly of formula $$(M''O)_n Fe_2O_3 \, (M'''_2O_3)_m$$

where $M''$ is a divalent metal such as Fe, Mg, Be, Mn, Zn, Co, Ba, Sr, and Cu, $M'''$ is a trivalent metal such as Al, Yb, Y, Mn, Cr or a lanthanide, and n and m are each zero or a positive number.

Preferably the magnetic particles are iron oxides of formula $(FeO)_n Fe_2O_3$ where n is in the range 0 to 1, typified by maghemite ($\gamma\text{-}Fe_2O_3$) and magnetite ($Fe_3O_4$) or are mixtures of such magnetic iron oxides.

A wide range of iron salts may be used as the source of $Fe^{III}$ and $Fe^{II}$ ions, e.g. $FeCl_2$, $FeCl_3$, $Fe^{III}$ citrate, $Fe^{II}$ gluconate, $FeSO_4$, $Fe_2(SO_4)_3$, $Fe^{II}$ oxalate, $Fe(NO_3)_3$, $Fe^{II}$ acetylacetonate, $Fe^{II}$ ethyldiammonium sulphate, $Fe^{II}$ fumarate, $Fe^{III}$ phosphate, $Fe^{III}$ pyrophosphate, ammonium $Fe^{III}$ citrate, ammonium $Fe^{II}$ sulphate, ammonium $Fe^{III}$ sulphate, and ammonium $Fe^{II}$ oxalate. The ratio of $Fe^{II}$ and $Fe^{III}$ ions should preferably be in the range 1:5 to 5:1.

Precipitation is initiated by setting the pH of the aqueous medium above the precipitation initiation threshold, generally by addition of a base, preferably an aqueous base such as an alkali metal hydroxide (e.g. sodium hydroxide, potassium hydroxide or lithium hydroxide) or ammonium hydroxide, particularly preferably concentrated ammonium hydroxide. The base added should have a pKb sufficient to bring the pH of the aqueous medium above the precipitation initiation threshold, e.g. to above 10.

The base is preferably added to an aqueous medium which contains the metal ions and the polymer. Alternatively, the base and polymer may be combined and the metal ions subsequently added. These additions may conveniently be effected by mixing aqueous solutions of the components at an elevated temperature, e.g. 40 to 95° C., preferably 50 to 60° C., with stirring.

It is believed that following initiation of precipitation, seed magnetic particle crystals form within amorphous paramagnetic domains of metal ions or metal hydroxides delimited by the branched polymer and that these amorphous domains transform into the fully formed magnetic particles. Thus particle formation may be allowed to proceed for a selected period of minutes to days, e.g. 1 minute to 24 hours, preferably 20 minutes to 10 hours, especially 1 to 5 hours.

Where the particle formation is effected at a temperature towards the upper end of the ranges specified herein, e.g. at 90° C., the medium is preferably kept at this elevated temperature for only a relatively short period, e.g. up to 2 hours.

If the base, precipitable metal ions and polymer are combined at a lower temperature and the medium is then heated to a higher temperature for magnetic particle formation to occur, then the rate of temperature increase should be carefully controlled, e.g. at 10–100 C.°/hour. Thus during particle formation the temperature of the aqueous medium is preferably raised in a controlled manner (e.g. with a temperature rise which is substantially linear with time), for example rising from a mixing temperature of 55° C. to a final temperature of 90° C. over a period of two hours.

After the particle formation period, it is particularly preferred to neutralize the reaction medium bringing it to a pH of for example 6.0 to 8.5. This can be done for example by cooling the medium to produce a set gel which can be washed until neutral, by neutralizing the medium with acid (acceptable acids include for example hydrochloric, sulphuric and nitric acids) or solid carbon dioxide or by applying a vacuum to remove the base if it has a high vapour pressure (eg. if it is ammonium hydroxide). The neutralized medium can be procesed further immediately.

For this neutralization step washing is particularly effective where the medium has been allowed to form a set gel and serves to remove excess metal salts and base. Washing may conveniently be effected with deionized water, preferably pre-cooled to 3 to 15° C., and is preferably continued until the pH is approximately neutral.

While one can simply sonicate the washed gel to break down the gel matrix without cleaving the polymer while still releasing polymer coated magnetic particles, it has been found that the particulate product has particularly beneficial properties if the polymer is cleaved to release the coated particles, e.g. by breaking down the polymer's molecular structure. Chemical breakdown may be effected using active chemical agents such as oxidants or bases but may also be effected using biochemical agents such as enzymes. For carbohydrate polymers such as starch one may conveniently cleave the polymer enzymatically using an enzyme such as an amylase, e.g. α-amylase. However it is especially preferred that polymer cleavage be effected using an oxidant. Oxidants which at trace levels are themselves biotolerable, or whose reduction products are similarly biotolerable, such as halogen oxyanions (e.g. alkali metal hypochlorites (such as sodium hypochlorite and calcium hypochlorite), periodates (such as sodium periodate), permanganates (such as $KMnO_4$), peroxides (such as $H_2O_2$), and enzymatic oxidants are preferred. Any excess oxidant that is used is preferably subsequently inactivated, e.g. by the addition of urea when hypochlorite is used as the oxidant. When polymer cleavage is effected using an oxidant, the magnetic particles thereby released possess a negative surface charge and particle agglomeration is further reduced.

The chemical agents used for polymer cleavage should preferably not be agents which will erode the magnetic particles or cause those particles to loose their magnetic properties. Accordingly, the use of acidic agents is generally undesirable.

The extent to which polymer cleavage occurs can be varied as desired in order to leave a smaller or larger amount of the residue of the polymer as a coating on the particles. It should also be noted that a coating is generally desirable and that as a result the overall particle size of the composite particles is larger than that of the magnetic particle cores. According to the selected cleavage technique, the residue left as a coating on the particles may be polymeric, oligomeric or even monomeric.

After polymer cleavage, the product is preferably washed free of contaminants using membrane filtration techniques, e.g. ultrafiltration or diafiltration.

The resultant overall particle size is generally in the range 1 to 300 nm, preferably 4 to 30 nm and especially preferably 8 to 20 nm. In this regard it may be noted that the preferred oxidant cleavage of the polymer tends to give smaller overall particle sizes than does the enzymatic cleavage procedure and that both give smaller sizes than does simple sonication of a gel matrix.

In one preferred embodiment, the composite particles can be prepared in a one-pot reaction which reduces overall reaction time, avoids work up and handling of intermediates and reduces heat stress on the core magnetic particles. In this embodiment, iron III and iron II salts (eg. chlorides) are dissolved in a starch-water solution and iron oxide particles are precipitated by the addition of a base (eg. aqueous ammonia). The reaction is allowed to run for 1 to 3 hours at 70–90° C. whereafter the quantity of excess base is reduced (eg. by applying a vacuum and/or nitrogen flushing over the hot reaction mixture where ammonia has been used). The pH is then reduced to below 8.2 or to the point where the reaction mixture loses its buffer capacity. Then the oxidation agent (eg. sodium hypochlorite) is added while the mixture is still hot (eg. 70–90° C.) and the oxidation is allowed to run at 70 to 90° C. until an acceptable composite particle size is reached. For a composite particle size in the range 10 to 20 nm the reaction time will be about 30 to 120 minutes. At 0.47 tesla and 40° C., the magnetic saturation moment should desirably be above 50 EMU/g FeOx, $r_1$ greater than 15 mM$^{-1}$.s$^{-1}$ and $r_2/r_1$ less than 2.3. The reaction mixture is then quenched with urea and filtered, eg. through 0.2 $\mu$m filters. The starch residues can be removed by diafiltration, eg. using a UF membrane with a molecular cut off of 20 to 200 kD.

The "core" magnetic particles preferably have particle sizes characteristic of single domain particles, e.g. a particle size of 1 to 50 nm, especially 1 to 20 nm, particularly 2 to 15 nm, and most preferably 4 to 12 nm. Indeed, in the composite particles produced by the process of the invention, the core crystals are generally substantially mono-sized, frequently being in the range 4 to 12 nm.

The process of the invention can be used to produce composite particles (i.e. cleaved polymer coated magnetic particles) having a sufficiently narrow size distribution to make subsequent size fractionation unnecessary, e.g. with at least 90% having particle sizes within 10 nm, preferably within 5 nm and especially preferably within 2 nm, of the intensity average particle size as measured by photon correlation spectroscopy. However, the particles will generally be filtered through a relatively large diameter filter, e.g. a 0.1 to 0.2 $\mu$m filter, to remove any occasionally occurring large polymer fragments or any biological or particulate contamination. (Particle size may be determined by electron microscopy.)

The composite particles produced by the process of the invention are themselves novel and form a further aspect of the invention. Viewed from this aspect the invention provides composite particles, preferably charged particles, having a mean overall particle size of 4 to 30 nm and comprising superparamagnetic inorganic core particles with a cleaved hydrophilic polymer coating material, preferably an oxidized carbohydrate material, especially a cleaved starch. Preferably, the majority of the composite particles will contain a single superparamagnetic core crystal.

Viewed from a further aspect the invention provides a contrast medium composition comprising a contrast effective amount of composite particles comprising superparamagnetic metal oxide core crystals and an organic coating, said core crystals having a mean diameter of 2 to 10 nm, preferably 4 to 8 nm, said particles having a mean diameter of up to 30 nm, preferably up to 15 nm, and said coating comprising oxidatively cleaved starch, preferably together with a functionalized polyalkylene oxide, eg. a phosphorus oxide terminal polyethylene glycol such as methoxy PEG phosphate.

The process of the invention can be effected in two discrete stages, with composite particles first being prepared for example by the conventional co-precipitation technique used for preparation of magnetic starch microspheres (MSMs) (see for example Schroder WO-89/03675), and with the polymer subsequently being cleaved to produce the composite particles according to the invention. The composite particles treated in this way may contain a plurality of magnetic crystals in each composite particle, with the polymer cleavage step generally serving to release coated monocrystals. Such a process forms a further aspect of the invention.

For certain applications it may be desirable to remove substantially all of the cleaved polymer coating from the magnetic particles and perhaps replace it with a different surface modifying agent. In this case, an oxidizing agent (preferably a nonionic oxidizing agent such as hydrogen peroxide) or an enzyme capable of digesting the cleaved polymer (eg. an amylase) may be used. The use of ionic oxidizing agents is less preferred since they reduce electrostatic stabilization and can promote aggregation of the magnetic particles as the sterically stabilizing cleaved polymer coating is removed. Before the cleaved polymer is removed, it is desirable to add a stabilizing agent, eg. an electrostatic stabilizing agent such as sodium diphosphate or sodium triphosphate which binds to the magnetic particles and imparts electrostatic stabilization to the suspension. The pH should desirably be maintained neutral or slightly alkaline (eg. by addition of sodium hydroxide) as acidic pH may cause flocculation by protonation of a phosphate stabilizing agent. Incubation of starch-derived cleaved polymer coated magnetic particles (produced by the methods of the Examples below) with sodium diphosphate and hydrogen peroxide at 50–60° C. for 3 to 24 hours was found to be sufficient to remove substantially all the residual starch-derived cleaved polymer coating. The resulting particles had a mean particle size of about 9 nm and were stable in suspension at ambient temperature and under steam sterilization conditions.

Such stable suspensions of such electrostatically stabilized magnetic particles are new and form a further aspect of the invention. Viewed from this aspect the invention provides an aqueous suspension of superparamagnetic inorganic core particles having a mean overall particle size of 4 to 30 nm, said particles being substantially freed of organic coating material and carrying a surface bound inorganic electrostatic stabilizing agent.

After polymer cleavage, and any desired washing and filtering of the released particles, the particles are preferably provided with a coating of a second material, e.g. in order to enhance biotolerability by reducing complement activation effects, to extend blood pool residue time, to provide a tissue targeting ability, to enhance shelf stability or to improve autoclavability.

Alternatively the second coating material may be introduced at an earlier stage, e.g. before magnetic particle formation or post magnetic particle formation and before polymer cleavage.

Particularly preferably, the second coating material is a coating of a natural or synthetic structural-type polysaccharide, a synthetic polyaminoacid or a physiologically tolerable synthetic polymer as described in PCT/GB94/02097 or of a stabilizer substance as described by Pilgrimm or Illum (supra). Particularly preferably the second coating material is a polyalkyleneoxide (e.g. a poloxamer, poloxamine, a polyethyleneglycol, etc.) or a heparinoid, and especially preferably such a material carrying a functional group, e.g. an oxyacid (e.g. sulphur, carbon or phosphorus oxyacid) function, which permits the coating material to bind chemically or adsorb to the composite particles and especially to the core magnetic particles. In this regard particular mention may be made of methoxy-PEG-phosphate (MPP) and other polyalkyleneoxide materials described by Pilgrimm in U.S. Pat. No. 5,160,725 and WO-94/21240. The beneficial effects of MPP can also be realized using hydrophilic polymers terminally functionalized with other siderophiles than the phosphate groups of MPP. One such group is salicylate. PEG can be functionalized with this by conjugation to 4-amino-salicylic acid or 5-amino-salicylic acid, both of which are essentially innocuous with a long history of biological use.

A further suitable second coating agent is a 3-hydroxy-4-pyridinone carrying a hydrophilic polymer such as PEG at the pyridine nitrogen. Simple analogs, such as 1,2-dimethyl-3-hydroxy-4-pyridinone, have been used clinically to void the human body of excess iron, for instance in people having received excessive red cell transfusions. These species have some of the largest known binding constants for $Fe^{III}$, namely a log-beta(3) on the order of 35. There are several synthetic pathways that may conveniently be applied here. The polymer (PEG) could be attached by alkylation of the nitrogen of 2-methyl-3,4-dihydroxypyridine. PEG could also be attached by alkylation of 2-methyl-3-hydroxypyridine, followed by oxidation of the resultant product in the 4-position. PEG could also be attached by reacting a PEG that bears a primary amino group with 3-hydroxy-2-methyl-4-pyrone, therein replacing the ring oxygen atom by a nitrogen and forming the desired 3-hydroxy-4-pyridionone in one step.

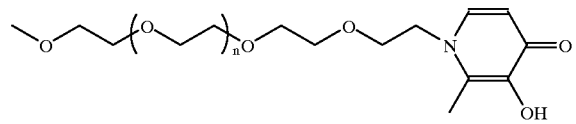

1-PEG-2-methyl-3-hydroxy-4-pyridinone

Further options for attaching PEG polymers to iron oxide surfaces would be to link them to one of the large group of bacterial siderophores, exemplified by ferredoxin/ferrioxamine. Ferrioxamine has an amino terminal function that may be used to attach a suitable PEG derivative by acylation or alkylation.

A further option for binding the second coating material to the oxide surface is to use oligomers or polymers of iron binding groups, e.g. phosphates such as diphosphate, triphosphate and higher polymers, rather than the monophosphate of MPP. Such oligo- and polyphosphates bind very strongly to iron oxide particles, probably due to the presence of multiple binding sites, and the conjugation reaction is simple and easy to perform. Thus for example in place of methoxy-PEG-phosphate referred to herein, eg. in the Examples below, one may use methoxy-PEG-diphosphate or methoxy-PEG-triphosphate. Oligo- and poly-phosphates, sulphates and sulphonates may also be used to conjugate other vector or reporter groups (as discussed further below) to the magnetic particles.

As an alternative to using the various phosphate binding groups discussed above for binding the second coating material or other vector and reporter groups to the oxide surface, one may instead use phosphonate binding groups, eg. one may use methoxy-PEG-phosphonate. This offers numerous potential advantages, particularly increased hydrolytic stability due to replacement of the P—O—C link of MPP by a P—C bond, potentially tighter binding to the oxide surface, and increased chemical stability allowing greater freedom to produce hetero-bifunctional PEG-phosphonates useful as linkers in producing magnetic crystal-linker-vector/reporter conjugates.

Thus for example heterobifunctional linkers such as

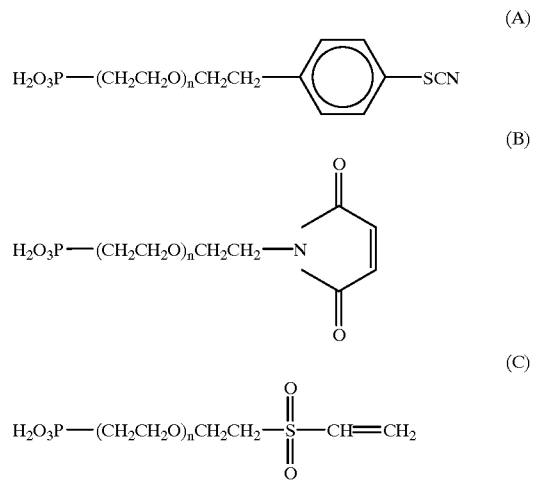

-continued

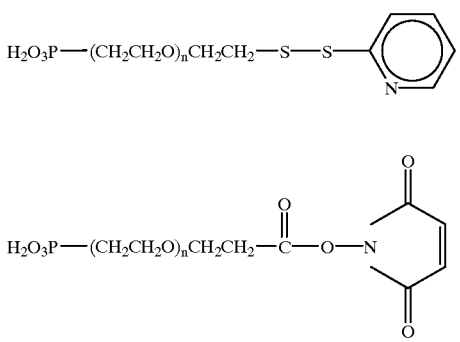

could readily be used to couple the magnetic particles to proteins, protein fragments, oligopeptides and other peptidic vectors. Thus the linkers of formula A to E may be coupled to such peptidic compounds with reactive thiol or amine groups and then coupled to the magnetic particles via the phosphonate groups.

Further suitable binding groups for attachment of PEG or other vector/reporter groups to the magnetic particles include other groups with high binding affinity for iron ions, eg. hydroxamate, catechol, ascorbate and deferrioxamine groups.

The molecular weight of the second coating material has been found not to be particularly critical and may conveniently be in the range 0.1 to 1000 kD, but materials having molecular weights of 0.3 to 20 kD, especially 0.5 to 10 kD and most especially 1 to 5 kD, are preferred, for example polyalkylene oxide materials having at least 60 alkylene oxide repeat units.

The weight ratio of the second coating material to the inorganic core particles is preferably in the range 0.02 to 25 g/g, especially 0.4 to 10 g/g and particularly 0.5 to 8 g/g.

One particular advantage that has been found for the doubly coated composite particles produced according to the process of the invention is that they may be sterilized by autoclaving (e.g. at 121° C. for 15 minutes) without unacceptable deterioration in particle size or size distribution. This is of particular importance since it means that earlier process steps need not be carried out under aseptic conditions and thus greatly improves production economics.

Besides providing a coating of a second coating material, other post-production modifications may be made to the composite particles produced according to the invention. Thus in particular the particles may be treated with a functional agent to conjugate or couple the residual carbohydrate coating, and biotargeting moieties (such as antibodies, antibody fragments, peptides or biomolecules such as insulin) or reporter groups (eg. groups detectable in diagnostic imaging modalities such as X-ray, MR, ultrasound, light imaging, etc.) may be conjugated to one of the coating materials using conventional chemical techniques. Further appropriate targeting vectors or immunoreactive groups are described for example in WO-93/21957.

Typically, the conjugates between the magnetic particles and such biotargeting (vector) and reporter groups may be represented by the formula

MP—X—L—V where MP is the magnetic particle (optionally with its cleaved polymer coating removed as described above); X is a group (anchor) capable of binding to the surface of the particle (eg. a phosphate, oligo- or polyphosphate, phosphonate, hydroxamate or other siderophile as discussed above); L is a bond or more preferably a linker group (preferably an organic chain of molecular weight 1000 to $10^6$ D, eg. a PEG group of mol. wt. 2 to 50 kD) linking at least one X group to at least one V group; and V is a vector or reporter group, ie. a group which modifies the biodistribution of the magnetic particle (eg. to produce preferential build up at selected organs, tissues or disease sites) or which is detectable by a diagnostic imaging technique (eg. a chelated heavy metal ion, heavy metal atom cluster, paramagnetic metal ion or metal radionuclide, or a gas microbubble or microbubble generator, a non-metal radionuclide, a non-metal non zero nuclear spin atom (eg. an F atom) besides hydrogen, a non-metal heavy atom (eg. I), a chromophore, a fluorophore, a drug, etc.).

A wide range of vectors and reporters may be conjugated to magnetic particles in this way. Examples of targeting vectors include: PEG (which causes extended blood pool residence); t-PA, streptokinase, and urokinase, either as whole proteins, or as selected fragments containing binding domains; peptides containing RGD and analogous platelet receptor binding motifs; and atherosclerotic plaque binding peptides (eg. the apolipoprotein B fragment SP-4). t-PA is available from Genentech. RGD peptides are described in a range of patent publications, eg. U.S. Pat. Nos. 4,589,881, 4,661,111, 4,614,517 and 5,041,380. One example of an RGD peptide that might be used is Gly-Arg-Gly-Asp-Ser-Pro-Ala-Ser-Ser-Ala-Tyr-Gly-Gly-Gly-Ser-Ala-Lys-Lys-CONH$_2$ which is conjugable via the Lys-Lys-CONH$_2$ terminus. This can be produced by standard oligopeptide synthesis techniques, eg. solid state peptide synthesis. SP-4, in the form (Tyr)-Arg-Ala-Leu-Val-Asp-Thr-Leu-Lys-Phe-Val-Thr-Gln-Ala-Glu-Gly-Ala-Lys-CONH$_2$ (where (Tyr) is added to permit radiolabelling with iodine) may be used with conjugation via the Lys-CONH$_2$ terminus. Again this can be produced by standard techniques.

Where V is a chelated metal, the linker will contain an appropriate chelating moiety, eg. a DTPA, EDTA, TMT, DO3A, etc. residue. Such groups are well known in the field of diagnostic imaging contrast agents and can be conjugated either via a backbone attached functionality (eg CH$_2$ØSCN) or via one of the metal coordinating groups (eg. CH$_2$COOH).

The metal ion will itself be chosen according to the imaging modality, eg. $^{90}$Y chelated by TMT for scintigraphy or TMT chelated europium for fluorescence imaging.

For X-ray imaging it is convenient to use an iodinated organophosphate (or phosphonate or oligo- or poly phosphate) as such compounds will both stabilize the magnetic particles and act as X-ray contrast agents (by increasing the radioopacity of the particles). Examples of suitable iodinated organophosphates would include

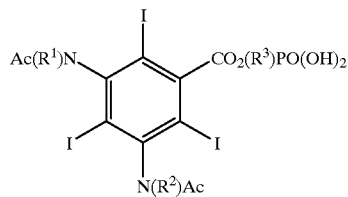

where $R^1$ and $R^2$ are optionally but preferably hydroxylated $C_{1-6}$ alkyl groups, and $R^3$ is a linker group, eg. providing a 1 to 6 carbon atom chain.

It is particularly preferred that the X—L—V compound should provide multiple anchor sites for attachment to the magnetic particle. Thus preferred X—L—V compounds are of formulae

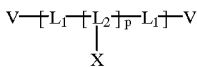

or

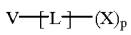

where $L_1$ and $L_2$ are components of linker L, and p is 2 or greater, eg. 2, 3, 4 or 5. Thus for example PEG based structures with 1 to 4 anchor groups might be as follows:

V—(PEG)—OC—CH$_2$—
N(CH$_2$X)CH$_2$(CH$_2$N(CH$_2$X)CH$_2$)$_r$CO(PEG)—V

[X(CH$_2$)$_s$]—CH$_2$—Y—(PEG)—V

V—PEG—CONH(CH$_2$)$_5$N(OH)CO(CH$_2$)$_2$CONH(CH$_2$)$_5$
N(OH)CO—(CH$_2$)$_2$CONH(CH$_2$)$_2$N(OH)COCH$_3$ where
r is 1, 2 or 3,
s is 1 to 6,
Y is CONH or NHCO,
(PEG) is a polyethyleneglycol chain, and
X is CONHOH, —CONH-bishydroxyphenyl or —CO—O-bishydroxyphenyl (with the two hydroxyl groups being on adjacent carbons).

Where a reporter or vector is conjugated in this fashion, the number per particle and the number per dose will clearly be selected such that sufficient vector is present to efficiently target the particles and/or that sufficient reporter is present that the particles may be detected by the chosen modality.

Thus one preferred embodiment of the process of the invention comprises the following sequential steps:
(i) combine in a heated aqueous solution a starch, ferrous and ferric salts and a base;
(ii) optionally, cool said solution to below 15° C. to allow a gel to set;
(iii) reduce the pH to within the range 6.0 to 8.5, this step optionally being performed before step (ii);
(iv) treat with an oxidant, e.g. a halogen oxyanion oxidation agent, to cleave the starch and release said particles;
(v) wash and filter the released particles;
(vi) optionally, react the released particles with a functionalized polyalkyleneoxide derivative to bind said derivative to said particles; and
(vii) optionally, autoclave sterilize the released particles.

Step (iii) can be performed for example by removing excess water and base (eg. ammonium hydroxide) under reduced pressure before step (ii) or by addition of acid (eg. HCl) to adjust for excess base before step (iv).

It has been found that composite particles, comprising inorganic core particles provided with a cleaved hydrophilic polymer coating and with a blood-lifetime-prolonging hydrophilic polymer bound to the inorganic particle surface, have significantly enhanced blood-lifetimes relative to comparable particles having only one of the two coatings. It is believed that this arises as a result of the cleaved polymer serving to shield the particle surface binding site of the blood-lifetime-prolonging polymer and so delaying in vivo cleavage of the blood lifetime-prolonging polymer from the inorganic particle. Such particles form a further aspect of the invention.

Viewed from this aspect the invention provides an injectable composite particulate agent comprising an inorganic particle core (preferably a metal or mixed metal oxide, especially a superparamagnetic iron oxide particle) having chemically or physically (but preferably chemically) bonded to the surface thereof a hydrophilic blood-lifetime-prolonging polymer (preferably a functionalized polyalkyleneoxide such as methoxy-PEG-phosphate, particularly preferably a terminally functionalized linear polymer, and preferably a polymer having a molecular weight below the kidney threshold, e.g. a molecular weight of 0.2 to 30 kD, especially 1 to 10 kD) and provided with a binding site shielding hydrophilic organic polymer coating, for example a cleaved branched carbohydrate, e.g. oxidized starch.

Such particles may be used as blood pool agents or alternatively may be conjugated to a biotargetting vector as described above. The particles moreover may be used in indirect lymphography, e.g. following iv or subcutaneous injection. While the inorganic core of these particles is preferably a superparamagnetic iron oxide, particles of other metal compounds may be used if desired, e.g. compounds incorporating a radionuclide or another therapeutically or diagnostically effective metal.

The relaxivity of the superparamagnetic crystal containing particles of the invention will vary with the size and composition of the core and of the coated particle (as well as with temperature and applied magnetic field). The $T_1$ relaxivity ($r_1$) may be as low as 5 and as high as 200, while $T_2$ relaxivity ($r_2$) may vary between 5 and 500 at 0.5 T (relaxivity given as $(mMFe)^{-1}(sec)^{-1}$). The $r_2/r_1$ ratio may vary from 1 to above 100, e.g. from 1 to 10, particularly 1.2 to 3 at 0.47T and 40° C. Small single crystal particles will have $r_2/r_1$ ratios in the lower range while large particles and multicrystal particles will show higher ratios. If the particles show superparamagnetic behaviour, the magnetization of the particles in the range 0T to about 1T will depend on crystal size, with larger crystals having significantly larger magnetization. At 1T the magnetization is about 20–100, preferably 30–90 emu/g iron oxide.

Where the superparamagnetic particles are produced by base precipitation of $Fe^{II}$ and $Fe^{III}$, the $r_2/r_1$ ratio at 0.47 T and 40° C. will generally be less than 3. As a result, in $T_1$-weighted imaging, the particles produced according to the invention are efficient as positive contrast agents. Furthermore, the magnetization curves for suspensions of such particles show that even at field strengths as high as 4T the particles are not fully magnetized. The incomplete magnetization of the particles at the field strengths conventionally used in MR imaging apparatus means that the magnitude of any susceptibility effects that may be present in the MR images is reduced. Moreover the relaxivity of the particles of the invention does not decrease as rapidly with increasing field strength as conventional iron oxide particles.

In conventional MR imaging, the drive for many years was towards the use of high field machines having primary magnetic field strengths of 1 to 1.5T. However the use of lower field machines is increasing and there is a developing need for positive MR contrast agents useful at the low field strengths of some commercial imagers, e.g. at 0.1 to 0.3T. This need is met by the particles of the invention which are at least three times more efficacious at these field strengths than the conventional metal chelate based positive MR contrast agents such as Magnevist and thus viewed from a further aspect the invention provides a method of contrast enhanced magnetic resonance imaging of a subject wherein a positive contrast agent is administered to a subject and an image of at least part of said subject is generated using an MR imaging apparatus, characterised in that said apparatus has a primary magnet having a field strength of below 0.3T, in that said positive agent comprises magnetic particles having a physiologically tolerable carbohydrate coating and in that said particles are incompletely magnetized at said field strength (e.g. magnetized to up to 90% of their maximum possible magnetization) and preferably are incompletely magnetized at field strengths of up to 2T, especially up to 4T.

Viewed from a further aspect, the invention provides diagnostic compositions comprising the particles of or produced according to the invention together with at least one physiologically acceptable carrier or excipient, e.g. water for injections.

The compositions of the invention may be in any conventional pharmaceutical form, e.g. suspension, emulsion, powder etc. and may contain aqueous vehicles (such as water for injections) and/or ingredients to adjust osmolality, pH, viscosity, and stability. Ideally, the composition is in suspension form with the suspension being isotonic and isohydric with blood. For example, an isotonic suspension can be prepared by the addition of salts like sodium chloride, low-molecular weight sugars like glucose (dextrose), lactose, maltose, or mannitol or a soluble fraction of the coating agent or a mixture of these. Isohydricity can be achieved by the addition of acids like hydrochloric acid or bases like sodium hydroxide if only a minor adjustment of pH is required. Buffers such as citrate, acetate, borate, tartrate, gluconate, zwitterions and Tris may also be used. The chemical stability of the particle suspension can be modified by the addition of antioxidants like ascorbic acid or sodium pyrosulphite. Excipients may also be added to improve the physical stability of the preparation. Most frequently used excipients for parenteral suspensions are surfactants like polysorbates, lecithin or sorbitan esters, viscosity modifiers like glycerol, propyleneglycol and polyethylene glycols (macrogols), or cloud point modifying agents, preferably non-ionic agents. (Cloud point modifying agents change the temperature at which non-ionic surfactant compositions undergo a phase separation which may result in flocculation).

The compositions of the invention will advantageously contain the magnetic metal oxide at a diagnostically effective metal concentration, generally 0.1 to 250 mg Fe/ml, preferably 0.5 to 100 mg Fe/ml, and especially preferably 1 to 75 mg Fe/ml.

The invention further provides a method of generating a contrast enhanced image of a human or non-human, preferably mammalian, body said method comprising administering to said body, preferably parenterally and especially preferably intravascularly, a suspension of a contrast agent according to the invention and generating an image of a least part of said body into which said agent distributes, e.g. by MR or magnetometry (e.g. using a SQUID detector or an array of SQUID detectors).

In an alternative aspect the invention also provides a method of determining distribution of a contrast agent according to the invention within a human or non-human, preferably mammalian, body, said method comprising administering a said agent to said body, preferably parenterally, and detecting a signal from said body emitted or modified by said agent, e.g. a radio active decay emission, a magnetic field distortion or a magnetic resonance signal.

Particularly preferably, the method of the invention involves imaging the vasculature, especially using $T_1$-weighted MR imaging. Image generation may be effected before any significant particle uptake by the liver or spleen occurs. With particles provided with a blood-lifetime-prolonging polymer coating, e.g. of methoxy PEG phosphate, image generation may conveniently take place within 24 hours, preferably within 4 hours and more preferably within 1 hour, of intravascular administration. In alternative embodiments of the method, following localized injection $T_2$ weighted images of lymphatic system may be generated or following injection into the vasculature $T_2$-weighted studies of liver or spleen or $T_2$-weighted diffusion studies may be effected.

For the method of the invention, the dosage used will be a contrast effective dosage for the imaging modality used. Generally this will lie in the region 0.05 to 30 mg Fe/kg bodyweight, preferably 0.1 to 15 mg Fe/kg and especially preferably 0.25 to 8 mg Fe/kg.

The invention also provides the use of the novel magnetic crystal materials for the manufacture of a diagnostic contrast agent composition for use in a method of diagnosis involving administration of said composition to a human or non-human animal body.

Besides being used as contrast agents, the composite particles of the invention may also be used in localized thermal treatments or hyperthermia applications—using their magnetic properties, energy may be transferred to the particles in vivo (eg. by exposure to a magnetic field of changing direction or field strength) and the energy loss from the particle to the surrounding tissue may be used to therapeutic effect, eg. to achieve a cytotoxic effect. This is of particular importance where the particles are conjugated to a targetting vector, eg. via a bifunctional linker such as a bifunctional polyalkylene oxide.

Similarly the particles may be used in iron therapy—in this case it is not necessary to develop the magnetic properties of the core crystals and these may be paramagnetic iron oxides provided with the cleaved polymer coating and optionally a second coating, eg. of MPP.

Various iron oxide preparations prepared according to the prior art are known to give significant adverse effects when administered intravascularly. The most frequently reported findings are suppression of systemic blood pressure and acute platelet depletion. It appears that these side effects may be physiological and haematological responses to particle induced activation of the complement system. While conventional iron oxide particles, such as magnetic starch microspheres (MSM), may strongly activate the complement cascade, the particles of the present invention have no or only minor influence on the number of circulating platelets while conventional preparations cause an acute marked and transient thrombocytopenia.

The particles of the present invention, whether with or without a second coating material (eg. MPP), have surprisingly been shown to have no effect on the complement system or on complement related parameters such as the blood pressure and platelet count. The selected coating material gives rise to a particle surface that will not trigger complement activation in a similar manner to the conventional particles.

The particles can easily be covered with a second coating material, e.g. a polymer which chemically or physically associates with the iron oxide (FeOx) surface (for example MPP). The particles are highly suitable for further surface modification or coating due to their large surface area and to the thin carbohydrate coating layer which permits terminally functionalized hydrophilic polymers such as MPP to penetrate and bind to or adsorb onto the surface of the core magnetic particle.

The FeOx particles have a lower magnetization than conventional iron oxide agents and the magnetization is not fully saturated within the imaging field range. This feature will reduce the appearance of susceptibility artifacts at high magnetic field strengths.

The particles have been found to have a significantly longer blood half-life (by a factor of 2 or more) in mice than conventional MSM particles produced by coprecipitation of starch and FeOx.

The blood kinetics of the particles can be further modified by adding the second coating material. Thus MPP coated particles, i.e. doubly coated particles, have been shown to have significantly longer blood half-lives (by a factor of 2 or more) in mice than particles without MPP coating or with methoxy-PEG (MeO—PEG) as an added excipient (MeO-PEG acts as an excipient and does not interact with the FeOx surface).

The MPP coated particles have been shown to have a significantly longer blood half-life (by a factor of 2 or more) in mice than nano-sized FeOx particles coated with MPP but without the primary coat of the cleaved polymer.

Both the singly coated and doubly coated particles according to the invention have been found to have no haematological effects in rats whereas conventional polysaccharide-FeOx preparations give rise to significant thrombocytopenia.

Moreover both the singly coated and doubly coated particles according to the invention have been found to have no effect on human complement whereas conventional starch-FeOx (MSM) particles are a potent complement activator.

The single crystal cored particles of the invention are particularly advantageous since they have a reduced tendency to aggregate so reducing the quantity of stabilizers (such as dextran) needed in the compositions of the invention and thereby reducing the possibility of toxicity problems.

To minimize storage and transportation problems, the particulate contrast agent produced according to the invention may conveniently be produced as a dry powder, eg. by spray drying or freeze drying, preferably under aseptic conditions. The dried agent forms a further aspect of the invention.

The various patent publications referred to herein are incorporated herein by reference.

The present invention will now be described in further detail in with reference to the following non-limiting Examples:

EXAMPLE 1

The gel preparation steps are: starch solution preparation and heating to 55° C., addition of iron chloride to starch solution, addition of ammonium hydroxide to iron/starch solution, heating of reaction mixture to 87–90° C. and product cooling/gel neutralization.

A. Preparation of Starch Solution
1. Suspend 50 grams of soluble potato starch (CAS No. 9005-84-9) in 850 grams of boiling deionized water and mix.
2. Bring to the boil and immediately on boiling place the starch solution in a 55° C. water bath.

B. Addition of Iron and Ammonium Hydroxide to Starch
1. Dissolve 9.0 grams of $FeCl_3.6H_2O$ and 3.3 grams of $FeCl_2.4H_2O$ (2:1 molar ratio FeIII to FeII) in a total volume of 50 mL of deionized water.
2. After starch solution has cooled to a steady 55° C., pour the iron solution into the starch solution, mix thoroughly and add 50 ml of 30% (conc.) $NH_4OH$.
3. Heat the resulting solution so as to increase the temperature to 89° C. over 2 hours and maintain at 89° C. for a further 50 minutes.
4. After the 170 minute heating on the water bath, a) chill overnight at 4° C. to set gel, or b) cool to ambient temperature and neutralize with acid (see below).

C. Gel Washing Procedure (Where Gel is Not Acid Neutralized)
Wash set gel by pumping cold deionized water through settled gel suspension until pH is less than 8.5.

D. Alternative Neutralization Process
Cool mixture to below 40° C., neutralize with acid.

E. Gel Oxidative Cleavage with Sodium Hypochlorite
A dose titration of the amount of sodium hypochlorite (hypo) per gram of gel can be done on a new lot to optimize production. Magnetic particle production is assessed by photon correlation spectroscopy (PCS) for size and dispersity, and by determination of water proton relaxation rates.

a. For example, 1.8 mls of 5% hypochlorite per 12.5 mgs Fe/5 gms of gel. Adjust volume of hypochlorite for concentration of available chlorine and mgs Fe in 5 grams of gel.
b. Weigh out gel, add hypochlorite and heat in water bath at 70° C. for 45 minutes. c. Add 8M urea (0.8 ml/5 gms of gel) after heating. Urea inactivates excess hypochlorite.
d. Diafilter using a membrane (MW cutoff<100 kD) until all free Fe and CHO is removed.

F. Analysis
Samples are then subjected to analysis. Material prepared in this way has the characteristics outlined in Table 1:

TABLE 1

| Analysis | Result | Scale up*** |
|---|---|---|
| Composition | | |
| Iron (Fe) Mossbauer spectroscopy | 6.4 mg/ml predominantly nano crystals of gamma-$Fe_2O_3$ | up to 95 mg/mL |
| Carbohydrate (CHO) | 3.6 mg/ml | |
| CHO:Fe (weight ratio) | 0.57 | 0.2–0.3 |
| PURITY | (Supernatant from particles centrifuged on CsCl density gradient of 1.4 g/ml) | (Gel Permeation Chromatography) |
| % Free Fe | 0% | |
| % Free CHO | 0% | 2% of area |
| SIZE (Iron Oxide Core) | | |
| Predicted from $r_2/r_1$ | 9 nm | 8 nm |
| NMRD* | 8 nm | 8 nm |
| LFI** | 6.24 ± 0.74 nm | |
| Calculated from Magnetization | 5.7–5.8 nm | |
| SIZE (Whole Particle) | | |
| Photon Correlation Spectroscopy | 11.5 nm | 10–12 nm |
| Sedimentation velocity | 42.6 Svedberg Units | |
| RELAXIVITY (at 4° C. and 0.47 T) | | |
| $r_1$ | 16.34 $(mM.sec)^{-1}$ | 20–23 $(mM.s)^{-1}$ |
| $r_2$ | 28.04 $(mM.sec)^{-1}$ | 34–38 $(mM.s)^-$ |
| $r_2/r_1$ | 1.72 | 1.6–1.7 |
| STABILITY++ at 4°0 C. | >6 months | |
| Saturation Magnetization | 60 emu/gm FeOx+++ | 80–90 emu/g Fe |

+++1 g FeOx is approximately 70% weight Fe
*Nuclear Magnetic Relaxation Dispersion
**Lattice Fringe Imaging
***Produced in larger scale
++Less than 5% sediments down on centrifugation at 12000 × g for 5 minutes.
% area = % total area under HPLC trace With NMRD, the longitudinal relaxation rate ($1/T_1$) is measured as a function of magnetic field strength in the range 2.35 Gauss to 1.2 Tesla. See for example Koenig et al. NMR Spectroscopy of Cells and Organisms, Vol. II, page 75, R. K. Gupta (Ed), CRC Press, 1987 and Koenig et al. Progress in NMR Spectroscopy 22: 487–567 (1990).

EXAMPLE 2

Magnetic particles were prepared according to Example 1 except that corn starch was substituted for potato starch.

It should be noted that use of materials other than soluble potato starch may require modification of the quantities of materials used for gel formation and degradation.

EXAMPLE 3

Magnetic particles were prepared according to Example 1 except that rice starch was substituted for potato starch.

EXAMPLE 4

Magnetic particles were prepared according to Example 1 except that they were not treated with hypochlorite (section D). Instead, samples of the gel (4, 8, 12 grams) were diluted with a phosphate buffered saline solution and the starch of the gel was subjected to enzymatic hydrolysis using 100 µg (at 0.7–1.4 units of activity per µg) of the enzyme alpha-amylase (EC 3.2.1.1) at ambient temperature for 16 hours. The resulting released particles were centrifuged at low speed to remove large aggregates and filtered through a 0.45 µm filter. This process produced particles with much larger overall sizes (range 10–110 nm) but with iron oxide cores of 6 nm.

EXAMPLE 5

Magnetic particles were prepared according to Example 1 except that they were not treated with hypochlorite (section D). Instead, 10 grams of the gel was subjected to sonication using a Branson sonifier fitted with a ¼ inch probe. Sonication was carried out continuously for 15 minutes. After being centrifuged at low speed to remove large aggregates and filtered through a 0.45 µm filter, the resulting released particles were also found to have a very much larger overall size (range 30–800 nm) but with similar sized iron oxide cores to those of Example 4.

EXAMPLE 6

Methoxy PEG phosphate (MPP) (mol. wt. 5 kD) was added to an aqueous suspension of particles produced according to Example 1 at the desired ratio of MPP to iron oxide (FeOx) (typically 1 to 2 gms MPP/gm Fe), incubated for 15 hrs at 37° C. with constant rotation and then stored at 4° C. until used.

If desired the particles can be autoclave sterilised at 121° C. for 15 minutes.

The particles may be coated analogously using chondroitin sulphate.

Alternatively, the MPP coated particles can be incubated at 75° C. for 12 hours or may be directly autoclaved at 121° C. for 10–20 minutes.

EXAMPLE 7

MPP coated particles were produced analogously to Example 6 using different molecular weight MPP (1.1, 2.1, 5.0 and 10.0 kD) and different coating ratios (0.02, 0.2, 0.4, 0.5, 0.8, 1.0, 1.2, 1.5, 1.6, 2, 2.5, 3, 4 and 8 g MPP/g FeOx).

EXAMPLE 8

Results of Animal Tests and Human Plasma Tests on Particles of Examples 1, 6 and 7

Mouse blood half-life ($T_{1/2}$) was determined for particles according to the invention having a range of MPP coating densities. Mice were injected via tail vein with 100 µL samples at 1 mg Fe/mL of the preparations of Examples 1, 6 and 7. At timed intervals, animals were euthanized, blood samples were collected and pooled from two mice and $1/T_1$ was measured. From $1/T_1$ values the half lives ($T_{1/2}$) were determined. The results are set out in Table 2 which includes for comparison the results for uncoated particles and conventional MSM particles:

TABLE 2

| gm MPP*/gm FeOx | $T_{1/2}$ (min) |
| --- | --- |
| 0 | 27.9 |
| 0.02 | 28.0 ± 3.2 # |
| 0.2 | 31.9 ± 3.3 |
| 0.4 | 39.1 ± 14.1 |
| 0.8 | 28.5 ± 1.3 |
| 1.6 | 69.3 ± 27.7 |
| 2 | 48.9 ± 3.8 |
| 4 | 45.6 ± 3.0 |
| 8 | 62.0 ± 5.6 |
| MSM | 3.8 |

*Mol. wt. 5 kD.
Mean ± an estimated standard error in the linearity of the $T_{1/2}$ curve fitting.
MSM: Conventional co-precipitated magnetic starch particles.

From Table 2 it is clear that MPP coating prolongs blood half-life significantly but that even uncoated particles according to the invention have much greater blood half-lives than the conventional particles.

Where a non-associating secondary coating agent was used in place of MPP, there was found to be no significant increase in blood half-life in mice. This was shown by a comparison of detected mouse blood half-lives for uncoated and MPP coated particles and for particles treated with methoxy PEG (mol. wt. 5 kD) and with a starch derivative Hetastarch. Unlike MPP, methoxy PEG does not bind chemically to or associate with the particles and so is simply present as an excipient. The results of the comparison are set out in Table 3:

TABLE 3

| Secondary Coating Agent/Excipient | $T_{1/2}$ (min) |
| --- | --- |
| MPP mol. wt. 5 kD, 8 g/g FeOx | 62.0 |
| MeO-PEG mol. wt. 5000, 8 gms/gm FeOx | 26.3 |
| HETASTARCH ®, 6% solution | 28.1 |
| None | 27.9 |

MPP coated and non-MPP coated particles were tested in rats for hematological effects.

Male rats were prepared with indwelling dosing and sampling catheters inserted in the right jugular vein. Approximately 24 hours prior to, and at approximately 3, 10 and 60 minutes and/or 24 hours following dosing, bloods samples were collected. Hematology parameters measured included: white blood cell and platelet count.

Unlike with dextran magnetite or MSM particles no incidence of transient thrombocytopenia was observed with the MPP-coated and MPP uncoated particles of the invention.

The MPP coated and non-MPP coated particles and MSM were tested on human plasma to determine the extent of activation of the terminal complement complex. Unlike MSM, the MPP coated and non-MPP coated particles did not cause activation.

EXAMPLE 9

Figure 2:
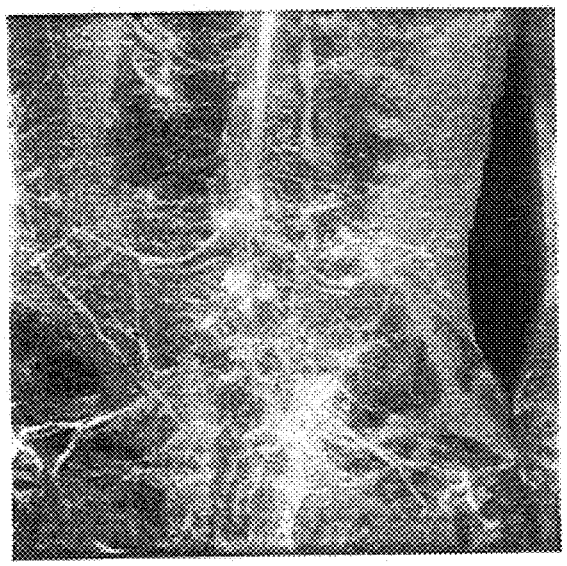
Figure 3:
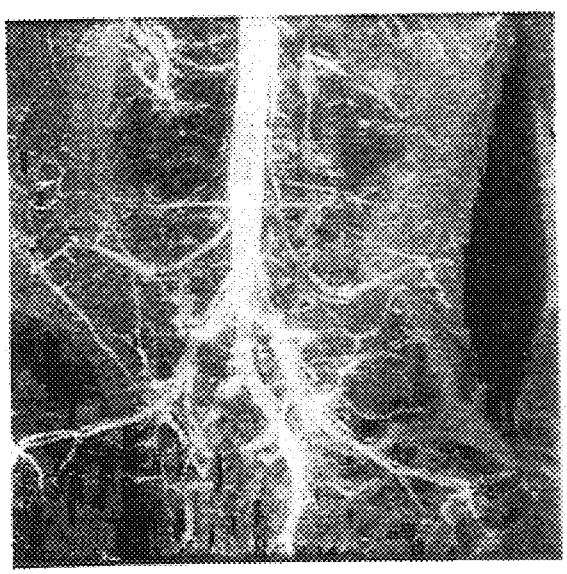

MPP coated particles produced according to Example 6 were administered into the rabbit at a dosage of 1 mg Fe/kg and fifteen minutes later at a dosage of 2 mg Fe/kg. Pre and post contrast $T_1$-weighted MR images were recorded at 1.5T, 3D TOF, TR/TE 25/5.6, flip angle 60°, and appear as FIGS. 1, 2 and 3 of the accompanying drawings. The enhancement of the vasculature is clear in both post-contrast images and, despite the combination of high dosage and high field, the image of FIG. 3 shows high vessel to tissue contrast without susceptibility artefacts.

EXAMPLE 10

Post-composite Particle Formation Polymer Cleavage (a) Synthesis of MSM

Starch (3 g, Reppe Glycose, Sweden) having a mean molecular weight of 70 kD was dissolved in water (10 mL). At a temperature of 60° C., $FeCl_3 6H_2O$ (2.7 g) and $FeCl_2 4H_2O$ (4.5g) was dissolved in the carbohydrate solution whereafter the mixture was slowly precipitated into 1.2 M NaOH (50 mL) at 60° C. while sonicating. The sonication was allowed to continue for another 10 minutes followed by a centrifugation at 5000 rpm for five minutes. The supernatant was collected and dialyzed against 0.9% NaCl. A magnetization curve revealed that the resultant starch particles were superparamagnetic and they exhibit a mean hydrodynamic diameter of 400 nm.

(b) Treatment of MSM with Sodium Hypochlorite

MSM particles (15.5 mgFe/mL, 1.70 mL) having a mean particle size of 400 nm were added to sodium hypochlorite (Fluka # 71696, 13.8% free chloride). The container was sealed tightly and heated at 70° C. for 45 minutes. The reaction mixture was cooled, 8M urea (0.17 mL) was added and the suspension was filtered (0.2 μm). The particles were purified with water using a Macrosep centrifugal concentrator (cutoff 100K) at 3000 rpm. The recorded particle size given as a function of the amount of sodium hypochlorite added is given in Table 4 below.

TABLE 4

Particle size of MSM before and after treatment with sodium hypochlorite

| Amount of NaOCl (mL) | Particle Size (mean, nm) |
|---|---|
| 0 | 400 |
| 0.063 | 88 |
| 0.100 | 76 |
| 0.300 | 70 |
| 0.500 | 68 |
| 1.000 | Aggregated 1) |

1) All starch cleaved, aggregation of naked iron oxide crystals

EXAMPLE 11

Formulated Products According to Examples 1 and 7

Table 5 presents details of properties of particles produced according to Example 1 (Composition A) and (1.2g MPP (2 kD)/g FeOx) (Composition B) and formulated with excipients (Tris (50 mM), mannitol (2.5%) and sodium hydroxide to pH 6–8) for administration.

TABLE 5

| ANALYSIS | COMPOSITION A | COMPOSITION B |
|---|---|---|
| COMPOSITION | | |
| Iron (Fe) | 30 mg/mL | 30 mg/mL |
| Carbohydrate (CHO):Fe ratio | 0.8 | 1.2 |
| MPP (2 kD) | 0 | 60 mg/mL |
| PURITY | (Gel Permeation Chromatography) | (Gel Permeation Chromatography) |
| % Free CHO | 10–12% of area | 10–12% of area |
| SIZE (Iron Oxide Core) | | |
| predicted from r2/r1 | 7 nm | 7 nm |
| NMRD | 7 nm | 7 nm |
| SIZE (whole particle) | | |
| Photon Correlated Spectroscopy | 9–11 nm | 11–13 nm |
| RELAXIVITY (at 40° C. and 0.47 Tesla | | |
| r1 | 19–20 (mM.sec)-1 | 19–21 (mM.sec)-1 |
| r2 | 30–32 (mM.sec)-1 | 30–33 (mM.sec)-1 |
| r2/r1 | 1.5–1.6 | 1.5–1.6 |
| Saturation Magnetization 0.45 Tesla | 90–100 emu/gm Fe | 90–100 emu/gm Fe |
| STABILITY | >3 months at 40° C. | >3 months at 40° C. |

Notes:
NMRD = Nuclear Magnetic Relaxation Dispersion
% area = % total of area under HPLC trace

EXAMPLE 12

(Best Mode for Preparing Particles Before MPP Coating)

(A) In a 22 L three necked flask equipped with an overhead mechanical stirrer and a condenser, 12.8 L of deionized water was heated to 95° C. whereafter a slurry of 800 g of soluble potato starch (Sigma, No. S-2630) in 1.6 L of deionized water was added with an agitation rate of 80–100 rpm. The resulting slightly cloudy solution was stirred for 10 minutes at ambient temperature and then cooled to 55° C. over a 30 minute period. A solution of 144 g iron(III) chloride hexahydrate and 52.8 g of iron(II) chloride tetrahydrate in 1.2 L deionized water was added, and then 3 minutes later 800 mL of 28% ammonium hydroxide was added in one portion. The agitation speed was lowered to about 60 rpm, and the black reaction mixture was stirred at ambient temperature for 15 minutes before heating gradually to 92° C. over a 60 minutes period. The temperature was maintained at 92–94° C. for three hours and progress of the reaction was measured by magnetic susceptibility measurements during and after the reaction. The excess ammonium hydroxide was removed by vacuum distillation. The concentration was cooled to about 20° C. and refrigerated to form a gel.

In all, four batches of gels were prepared with the largest batch using 800 g of potato starch.

TABLE 6

Preparation of Gel

| Batch | Starch (g) | FeCl$_3$ 6H$_2$O (g) | FeCl$_2$ 4H$_2$O (g) | NH$_4$OH (mL) | Reaction Volume (L) | Gel Weight (kg) | Fe, by XRF* (g/kg) | M (emu/ mg FR) | M$_{sus}$ (×10$^{-4}$ emu/Oe.cm$^3$) |
|---|---|---|---|---|---|---|---|---|---|
| 1 | 600 | 108 | 39.6 | 600 | 12 | 9.8 | 3.33 | 0.0932 | 0.69 |
| 2 | 600 | 108 | 39.6 | 600 | 12 | 9.8 | 3.35 | 0.0954 | 0.71 |
| 3 | 600 | 108 | 39.6 | 600 | 12 | 9.8 | 3.36 | 0.0924 | 0.69 |
| 4 | 800 | 144 | 39.6 | 800 | 12 | 13.7 | 3.30 | 0.0955 | 0.70 |

*XRF = X-ray fluorescence spectroscopy (B) The gel was washed with cold water to remove ammonium chloride obtained in the iron oxide formation plus residual ammonium hydroxide. These compounds would otherwise react with sodium hypochlorite used to digest the starch in step C, requiring a much greater amount of hypochlorite for the hypochlorite step.

Gel washing was-accomplished with repetitive water addition/removals in a stirred reactor which was kept near 5° C. to minimize gel dissolution. The gel was stirred (briefly and slowly) in about 2 volumes of cold deionized water and then allowed to settle (about 1 hour). A dark supernatant layer separated from a very dark gel layer was removed by suction (visual observation of the layers). Addition of an equal amount of water, brief slow agitation, settling and separation was repeated until a conductivity of 0.5 mmho was obtained. A total of about 8 volumes of water was necessary to wash the gels, with the recovery of iron about 80%.

rite. The amount of hypochlorite used for the oxidation was determined by carrying out small scale (50–100 g of gel) oxidation experiments and measuring relaxivity (r1, r2 and r2/r1) and particle sizes.

The washed gel was warmed to 45° C. and treated with 12% sodium hypochlorite solution. The temperature of the reaction mixture dropped by few degrees (because of addition of refrigerated hypochlorite). The temperature of the reaction mixture was allowed to increase to about 45° C. The reaction was heated to 55° C. over 30 minutes, at which point an exothermic reaction was observed, with temperature increasing by about 15° C. over a 15 minute period. After the exotherm subsided, the temperature of the reaction was adjusted to 70° C. and maintained for 45 minutes. The hazard evaluation of this step using RCI calorimeter confirmed a modest (15° C.) but controllable exotherm for this reaction. The reaction mixture was allowed to cool to room temperature and filtered through a Millipore 0.2 micron

TABLE 7

Washed Gel

| Batch | Weight charged (kg) | Water total (L) | Turn-overs | Final Weight (kg) | Fe (g) | Fe Recovery (%) | Conductivity initial (mmho) | Conductivity final (mmho) |
|---|---|---|---|---|---|---|---|---|
| 1 | 1.7 | 15 | 7 | (centrifuged) | 6.1 | 78 | 4.8 | 0.3 |
| 2 | 9.5 | 80 | 5 | 14.5 | 26.5 | 81 | 5.2 | 0.5 |
| 3 | 9.5 | 80 | 4 | 11.2 | 24.5 | 77 | 4.7 | 0.5 |
| 4 | 13.3 | 106 | 5 | 16.4 | 36.9 | 83 | 4.8 | 0.3 |

(C) This step involves conversion of washed gel to particle dispersion by oxidation of the starch matrix. This was accomplished by treatment of the gel with sodium hypochlonominal filter cartridge. The largest oxidation was carried out on 15 kg of gel (34 g of Fe) and recovery was quantitative.

TABLE 8

Particle Dispersion

| Batch | Weight Charged (kg) | 12% NaOCl (L) | Urea Quench (g) | Final Volume (L) | Fe (g) | Brookhaven (nm) | r1 (mM.s)$^{-1}$ | r2 (mm.s)$^{-1}$ | r2/r1 |
|---|---|---|---|---|---|---|---|---|---|
| 1 | 3.0 | 0.63 | 20 | 3.5 | 5.5 | 11.1 | 13.37 | 23.1 | 1.68 |
| 2 | 6.5 | 1.83 | 42 | 8 | 11.8 | 11.8 | 14.5 | 24.8 | 1.68 |
| 3 | 10 | 2.25 | 112 | 12 | 22 | 12.4 | 14.9 | 25.0 | 1.68 |
| 4 | 15 | 3.00 | 80 | 18 | 34 | 12.7 | 21.0 | 36.2 | 1.71 |

(D) This step involves removal of residual starch, free iron and other reactants after the hypochlorite oxidation. Millipore, prescale TM TFF 100K regenerated cellulose membrane cartridge filters were used to achieve the desired results. The purity of the particles was monitored by GPC. The purity of the final product after ultrafiltration was in the range of 97–99% (GPC).

TABLE 9

Final Product

| Batch | Volume charged (L) | Filter Media | Water, total (L) | Final weight (kg) | Fe by ICP Ig) | Fe Recovery (%) |
|---|---|---|---|---|---|---|
| 1 | 2 | Millipore 100 K, 1 ft² regenerated cellulose | 25 | 670 | 2.2 | 67 |
| 2 | 6 | Millipore 100 K, 6 ft² regenerated cellulose | 45 | 671 | 8.8 | 70 |
| 3 | 12 | Millipore 100 K, 6 ft² regenerated cellulose | 60 | 980 | 13.7 | 73 |
| 4 | 18 | Millipore 100 K, 6 ft² regenerated cellulose | 100 | 1674 | 27.7 | 82 |

The final analytical date for all four batches are summarized in Table 10 below.

(E) Subsequent PEG Coating

The particles produced by steps (A) to (D) above may if desired be PEG coated, preferably with methoxy PEG phosphate (MPP) of molecular weight 2000 D at a coating ratio of 1.2 g MPP per gram FeOx.

The particles, with or without such a PEG coating may be formulated for administration with 50 mM Tris buffer, and 2.5% mannitol with pH adjusted to 6 to 8 with sodium hydroxide.

TABLE 10

Analytical Results

| Batch | 1 | 2 | 3 | 4 |
|---|---|---|---|---|
| Purity (%, GPC) | 97.2 | 98.1 | 99.0 | 99.2 |
| Iron (mg/ml, (ICP)) | 3.3 | 13.1 | 13.7 | 16.5 |
| r2/r1 | 1.67 | 1.66 | 1.65 | 1.64 |
| r1 (mM.s)$^{-1}$ | 19.6 | 18.9 | 20.0 | 21.3 |
| r2, (mM.s)$^{-1}$ | 32.7 | 31.3 | 33.0 | 35.0 |
| Magnetization: (emu/mg Fe) | 0.0762 | 0.0795 | 0.0801 | 0.0826 |
| Particle size (nm, Brookhaven) | 12 | 10 | 10 | 11 |
| Mobility (mV$^{-1}$s$^{-1}$ × E08) | −3.02 | −3.02 | −3.04 | −2.92 |
| pH | 4.1 | 4.0 | 4.0 | 4.0 |
| Carbon/Iron ratio | 0.52 | 0.28 | 0.30 | 0.28 |
| Appearance | Non-viscous, dark red to brown | Non-viscous, dark brown | Non-viscous, dark brown | Non-viscous, dark brown |

EXAMPLE 13

Preparation of Diethyl 2-(3,5-Bis-acetylamino-2,4,6-triiodobenzoyloxy)ethylphosphonate To a stirred solution of sodium diatrizoate (7.1 g, 11.2 mmol) in dry dimethylformamide (50 ml) at room temperature under a blanket of argon was added a solution of diethyl 2-bromoethylphosphonate (3.02 g, 12.3 mmol, 1.1 eq.) in dimethylformamide (10 ml). After stirring for 12 hours, the solvent was evaporated under vacuum to give a white solid that was washed with 300 ml of saturated aqueous $NaHCO_3$, and then extracted with a 2:1 mixture of chloroform-ethanol (3×200 ml). The organic extract was dried ($MgSO_4$), filtered, and evaporated under vacuum to give 3.61 g (41%) of product as a white solid. Recrystallization from acetonitrile gave analytically pure material; mp 249–251° C.; MH$^+$ (779). The $^1$H-NMR (300 MHz) spectrum was consistent with the desired material.

Calculated for $C_{17}H_{22}I_3PN_2O_7$: C, 26.24; H, 2.85; I, 48.93; N, 3.60; Found: C, 26.26; H, 2.70; I, 49.05; N, 3.50.

EXAMPLE 14

Preparation of 2-(3,5-Bis-acetylamino-2,4,6-triiodobenzoyloxy)ethylphosphonic acid To a stirred suspension of diethyl 2-(3,5-bis-acetylamino-2,4,6-triiodobenzoyloxy)ethylphosphonate (3.1 g, 3.98 mmol) in dry dichloromethane (40 ml) at room temperature under an atmosphere of nitrogen was added 1.5 ml (10.56 mmol, 2.65 eq.) of trimethylsilyl iodide. After stirring for 12–14 hours, a viscous slurry was observed, whereupon an additional 40 ml of dichloromethane was added and stirring was continued for 6 hours. Water (4 ml) was then added and the reaction was stirred for 10 minutes. Methanol (40 ml) was then added and the resulting red solution was concentrated under vacuum to give 3.42 g of the desired crude product as a yellow solid. The crude product was dissolved in 20 ml of a solution of 10% methanol-90% water and the solution was passed through a $C_{18}$ ion exchange column, eluting with 50 ml of the methanol-water solution. The filtrate was concentrated under vacuum to give 0.48 g (14%) of the desired phosphonic acid as a white solid, mp >220° C. (dec. ~250° C.); MH$^+$(723). The $^1$H-NMR (300 MHz) spectrum was consistent with the desired material.

Calculated for $C_{13}H_{14}I_3PN_2O_7$: C, 21.63; H, 1.95; I, 52.73; N, 3.88; P, 4.29; Found: C, 21.29; H, 1.95; I, 52.44; N, 3.71; P, 4.31.

The compound of Example 14 may be used for coating magnetic particles produced according to the previous Examples.

EXAMPLE 15

Synthesis of Methoxy-PEG(2K)-Phosphonate

Step 1

Methoxy-PEG(2K)—OH (21.60 g) was refluxed in 108 ml of toluene with azeotropic removal of water for several hours. The cooled solution was treated dropwise with a mixture of thionyl chloride (7.88 mL) and DMF (0.313 mL) then heated to reflux for 4 hours. The reaction mixture was concentrated under reduced pressure and the residual light yellow solid taken up in 108 mL of water and washed twice with ether. The aqueous solution was extracted twice with chloroform and the combined extracts were dried over anhydrous magnesium sulfate and concentrated to 19.90 g of methoxy-PEG(2K)—Cl.

Step 2

A mixture of methoxy-PEG(2K)—Cl (18.51 g) and triethylphosphite (185 mL) was refluxed for 4 days. A precipitate formed upon cooling to room temperature; the precipitate was collected by filtration, washed with ether and vacuum dried to 18.16 g of methoxy-PEG(2K)—P(O) (OEt)$_2$. $^1$H NMR (CDCl$_3$; 300 MHz): 4.10 ppm (m, —P (O) (OC$\underline{H}_2$CH$_3$)$_2$); 3.65 ppm (s, (—C$\underline{H}_2$C$\underline{H}_2$O—)$_n$) ; 3.38 ppm (s, —OC$\underline{H}_3$); 2.13 ppm (doublet of triplets, —CH$_2$C$\underline{H}_2$P(O) (OCH$_2$CH$_3$)$_2$); 1.33 ppm (t, —P(O) (OCH$_2$C$\underline{H}_3$)$_2$).

Step 3

A solution of methoxy-PEG(2K)—P(O)(OEt)$_2$ (5.02 g) in 100 mL of methylene chloride was treated dropwise with 28 mL of a solution prepared from 24.15 g of bromotrimethylsilane and 157 mL of methylene chloride. The reaction mixture was stirred at room temperature for 16 hours, then concentrated to a white solid. The white solid was treated with 50 mL of methanol for 2 hours, then concentrated to 4.57 g of product as a white solid. $^1$H NMR (CDCl$_3$; 300 MHz): 8.20 ppm (br s, —P(O) (O$\underline{H}$)$_2$); 3.65 ppm (s, (—C$\underline{H}_2$C$\underline{H}_2$O—)$_n$); 3.38 ppm (s, —OC$\underline{H}_3$); 2.17 ppm (doublet of triplets, —CH$_2$C$\underline{H}_2$P(O) (OH)$_2$).

EXAMPLE 16

Preparation of Methoxy-PEG(2K)-Phosphonate/ Superparamagnetic Iron Oxide Conjuaate A mixture of Methoxy-PEG(2K)-Phosphonate (0.448 g); 3.42 mL of a 93.7 mg Fe/mL suspension of an iron oxide product according to Example 12 and water to a total of 20 mL was incubated at 37° C. for 20 hours. The reaction mixture was placed in a 50 mL Amicon stirred cell equipped with a YM-30 membrane and diafiltered against water then filtered through a 0.2 μm nylon filter. The sample was found to contain 13.3 mg Fe/ml by ICP analysis; 0.34 mg/ml of unbound Methoxy-PEG(2K)-Phosphonate and 1.42 mg/ml of bound Methoxy-PEG(2K)-Phosphonate.

EXAMPLE 17

Preparation of Methoxy-PEG(5K)-Thiol/ Superparamagnetic Iron Oxide Conjugate

A mixture of Methoxy-PEG(5K)-Thiol (0.438 g); 1.67 mL of a 93.7 mg Fe/mL suspension of an iron oxide product according to Example 12 and water (10 mL) was incubated at 37° C. for 22 hours. The reaction mixture was placed in a 50 mL Amicon stirred cell equipped with a YM-30 membrane and diafiltered against water then filtered through a 0.2 μm nylon filter. The sample was found to contain 13.47 mg Fe/ml by ICP analysis; 0.23 mg/ml of unbound Methoxy-PEG(SK)-Thiol and 5.46 mg/ml of bound Methoxy-PEG(5K)-Thiol.

EXAMPLE 18

Preparation of Iron Oxide Particle Suspensions with and without MPP Coating

Without MPP

Start by adding ~70% of the batch volume of Water for Injection to a glass or glass-lined manufacturing tank. With constant mixing, add and dissolve mannitol. The final concentration of mannitol can range from 1 to 5% w/v with 3.5% w/v being typical. With constant mixing, add and dissolve tromethamine. The final concentration of tromethamine can range from 10 to 100 mM with 50 mM being typical. With constant mixing, add iron oxide bulk suspension (produced according to Example 12). The final concentration of iron oxide can range from 0.1 to 10% w/v iron with 3% being typical. Check the pH of the bulk suspension. If necessary, adjust the pH to 8.1–8.3 (target 8.2) with either 0.1 N NaOH or 0.1 N hydrochloric acid. While continuing mixing, adjust the bulk suspension to 100% of the final volume with Water for Injection. The suspension prepared can be sterilized by steam heat at 121° C. for 10 to 50 F$_o$ with 15 F$_o$ being typical. The final suspension can have a pH ranging from 5 to 8 with 7 to 7.5 being the typical range.

With MPP

Starting by adding ~25% of the total batch volume of Water for Injection to an appropriate tared manufacturing tank. With continuous mixing, add methoxy-poly(ethylene glycol)(2000) phosphate and dissolve. The final MPP/Fe ratio can range from 0.1 to 5 with 1.5 being typical. With continuous mixing, add and dissolve tromethamine. The final concentration of tromethamine can range from 10 to 100 mM with 50 mM being typical. With mixing, add and dissolve mannitol. The final concentration of mannitol can range from 1 to 5% w/v with 2.5% being typical. Weigh out proper amount of iron oxide suspension (produced according to Example 12) in a suitable container. With mixing, add the solution containing MPP, mannitol, and tromethamine slowly to the iron oxide suspension. The final concentration of iron oxide can range from 0.1 to 10% w/v iron with 3% being typical. Check the pH of the suspension. Adjust the pH to 8.4–9.0 with 0.4 N sodium hydroxide. While continuing mixing, adjust the suspension to 100% of the final volume with Water for Injection. The suspension prepared as described can be sterilised by steam heat at 121° C. for 10 to 50 F$_o$ with 15 F$_o$ being typical. The MPP binding to iron oxide is completed during the steam sterilisation. Alternatively, the suspension can be incubated at 60 to 95° C. for 2–4 hours to complete the MPP binding to the iron oxide. The final suspension can have a pH ranging from 5 to 8 with 7 to 7.5 being the typical range.

EXAMPLE 19

Preparation of Naked Iron Oxide Nanocrystals (a) Removal of Starch-derived Polymer Coating from Iron Oxide without Adding Stabilizer A test was conducted to determine whether, starting from oxide suspensions produced according to Example 12, stable suspensions of iron oxide nanocrystals without a polymer coating can be prepared without any replacement stabilizer. 0.5 ml of 30% hydrogen peroxide was added to 0.5 ml aliquots of iron oxide suspension. The sample was incubated at 55° C. with constant stirring and a pH electrode was used to monitor its pH. As the oxidation reaction progressed, the sample pH drifted downward. The sample pH was maintained within the range of 6.5–7.5 by adding 1 N NaOH. Within 3 hours of incubation, the sample flocculated indicating that the iron oxide particle suspension, once stripped of its polymer coating, is unstable and formed large aggregates.

(b) Trial with Monophosphate

To test the effectiveness of monophosphate as surface modifier for stabilisation of naked iron oxide nanocrystals (nions), a study was conducted where 0.5 ml aliquots of iron oxide suspension were mixed with various concentrations of trisodium phosphate. 0.5 ml of hydrogen peroxide was then added to each sample. The samples were incubated at 55° C. to oxidize the starch-derived polymer coating (SDPC).

| Sample # | [Na$_2$HPO$_4$] (mM) |
|---|---|
| 0 | 0 |
| 1 | 1.7 |
| 2 | 8.3 |
| 3 | 16.6 |
| 4 | 33.3 |
| 5 | 50 |
| 6 | 66.7 |
| 7 | 83.3 |
| 8 | 166 |
| 9 | 250 |
| 10 | 333 |

All samples flocculated after 5 hours of incubation at 55° C., indicating that monophosphate is not a satisfactory surface modifier and stabilizer for naked ferrons (c) Diphosphate as Surface Modifier and Stabilizer The effectivness of diphosphate (also known as pyrophosphate) as a surface modifier of iron oxide particles was studied using tetrasodium pyrophosphate (anhydrous) and a method similar to that used with the monophosphate. The samples were incubated at 55° C. to oxidize the starch-derived polymer coating (SDPC). After incubation at 55° C. for 5 hours, Samples 2–7 remained suspended. Their mean particle sizes were measured and shown in the table below.

| Sample # | $[Na_4P_2O_7]$ (mM) | Mean Particle Size (nm) |
|---|---|---|
| 0 | 0 | * |
| 1 | 2.5 | 11.6 |
| 2 | 6.3 | 9.5 |
| 3 | 12.5 | 9.3 |
| 4 | 18.8 | 9.7 |
| 5 | 25.1 | 9.1 |
| 6 | 25.1 | 9.6 |
| 7 | 62.7 | 9.7 |
| 8 | 125.4 | * |
| 9 | 188.1 | * |
| 10 | 250.7 | * |

*Samples flocculated.

The small particle sizes reflect the removal of the starch-derived polymer coating material. This data indicates that pyrophosphate in the concentration range of approximately 2 to 60 mM is a satisfactory surface modifier and stabilizer for naked iron oxide crystals.

(d) Triphossphate as Surface Modifier and Stabilizer

A study was carried out to test triphosphate as stabilizer. Pentasodium triphosphate hexahydrate from Sigma was used. To 3.75 ml of iron oxide suspension was added 5.25 mM of sodium triphosphate, 3.75 ml water and 7.5% of 30% hydrogen peroxide. The mixture was incubated at 60° C. for 3 hours. The suspension did not show any sign of flocculation and the particle size was measured to 9 nm. Again, the smaller mean particle size reflects the removal of the coating starch-derived material. This data indicates that triphosphate is a satisfactory surface modifier and stabilizer for naked iron oxide crystals.

(e) Tetraphoshate as Surface Modifier and Stabilizer

A similar study was carried out to test tetraphosphate. The hexammonium tetrapolyphosphate salt from Sigma was used. The results are summarized in the following table.

| Sample # | $[P_4O_{13}]$ (mM) | Mean Particle Size (nm) |
|---|---|---|
| 0 | 0 | * |
| 1 | 2.5 | 27.3 |
| 2 | 5 | 9.5 |
| 3 | 10 | 10.1 |
| 4 | 20 | 9.3 |

*Samples flocculated.

Again, the small particle sizes of Samples 2–4 after incubation reflect the removal of the starch-derived coating material. This data indicates that tetraphosphate is also a satisfactory surface modifier and stabilizer for naked iron oxide crystals.

Characterization of Naked Iron Oxide Nanocrystals

Suspensions of naked iron oxide nanocrystals (nions) were prepared using sodium pyrophosphate. Upon completion of the oxidation, the suspension was diafiltered against water to remove fragmented starch and residual hydrogen peroxide. The resulting suspension was characterized by several analytical techniques as summarized below.

(a) GPC: Gel permeation chromatography (GPC) indicate that the naked iron oxide nanoparticles (NION) show a sharp peak with no trailing of starch-derived polymers.

(b) Total Organic Carbon: Analysis of two separate nion preparations showed only baseline level of total organic carbon, indicating essentially complete removal of the polymer coating.

| Sample | TOC (ppb) | Fe Concentration |
|---|---|---|
| Water Blank | 159 | — |
| Nion | 156 | 2.6 µg/ml |
| Water Blank | 144 | — |
| Nion | 211 | 30 µg/ml |
| Example 12 | 4060 | 18 µg/ml |

(c) Capillary Electrophoresis: Analysis of nions showed an electrophoretic mobility of $-3.4 \times 10^{-4}$ $cm^2 v^{-1} s^{-1}$ which is slightly more negative than that of the product of Example 12 ($-3.0 \times 10^{-4}$ $cm^2 v^{-1} s^{-1}$). This is consistent with the negative electrostatic charges added to the particles by the polyphosphates.

(d) Relaxivity and Magnetic Saturation: The magnetic relaxivity was determined. The $r_1$ and $r_2$ were 22.5 and 34.4 $mM^{-1} s^{-1}$ respectively giving a value of 1.53 for $r_2/r_1$. These values are generally quite similar to those of the product of Example 12.

(e) Stability under Steam Sterilization: Nion suspensions were steam sterilized at 121° C. for 20 min and showed no detectable change in particle size.

What is claimed is:

1. A process for producing composite magnetic particles, said process comprising:

(a) forming iron oxide particles within a polysaccharide containing aqueous medium; and (b) cleaving said polysaccharide whereby to release said composite particles, said process comprising the following sequential steps:

(i) combining in a heated aqueous solution a polysaccharide, ferrous and ferric salts, and a base;

(ii) optionally, cooling said solution to below 15° C. to allow said medium to set;

(iii) reducing the pH to within the range 6.0 to 8.5, this step optionally being performed before step (ii);

(iv) treating with an oxidant to cleave the polysaccharide and release said particles;

(v) washing and filtering the released particles;

(vi) optionally, reacting the released particles with a functionalized polyalkyleneoxide to bind said functionalized polyalkyleneoxide to said particles; and (vii) optionally, autoclave sterilizing the released particles.

2. A process as claimed in claim 1 wherein said medium is a gel.

3. A process as claimed in claim 2 wherein said gel contains anionic sites.

4. A process as claimed in claim 1 wherein said iron particles are superparamagnetic.

5. A process as claimed in claim 1 wherein said polysaccharide is a starch.

6. A process as claimed in claim 1 wherein cleavage of said polysaccharide is effected by treatment of particles which comprise a plurality of said iron oxide particles within a matrix of said polysaccharide.

7. A process as claimed in claim 1 wherein said step (vi) is not optional and attaches to said composite particles a coating of functionalized polyalkyleneoxide.

8. A process as claimed in claim 7 wherein said functionalized polyalkyleneoxide is present in said medium before step (iv).

9. A process as claimed in claim 1 wherein said aqueous medium further contains a linear polymer.

10. A process as claimed in claim 1 wherein said polysaccharide is cleaved following formation of magnetic particle-polysaccharide composite particles.

11. A process as claimed in claim 1 wherein the majority of composite particles so released contain a single iron oxide particle.

12. A process as claimed in claim 1 wherein the cleavage step (iv) is performed in two steps with the second cleavage step being so effected as to remove substantially all of said polysaccharide from the magnetic particles, said second cleavage step being effected in the presence of or following the addition of a stabilizing agent which binds to the magnetic particles.

13. A process as claimed in claim 1 wherein process steps (a) and (b) are effected in the same reaction vessel.

* * * * *